(12) United States Patent
Chung et al.

(10) Patent No.: US 11,672,749 B2
(45) Date of Patent: Jun. 13, 2023

(54) PEPTIDE EXHIBITING WRINKLE-IMPROVING ACTIVITY AND USES THEREOF

(71) Applicant: CAREGEN CO., LTD., Anyang-si (KR)

(72) Inventors: Yong Ji Chung, Yongin-si (KR); Eun Mi Kim, Yongin-si (KR); Eung Ji Lee, Anyang-si (KR)

(73) Assignee: CAREGEN CO., LTD., Anyang-si (KR)

( * ) Notice: Subject to any disclaimer, the term of this patent is extended or adjusted under 35 U.S.C. 154(b) by 0 days.

(21) Appl. No.: 17/389,731

(22) Filed: Jul. 30, 2021

(65) Prior Publication Data

US 2021/0369585 A1    Dec. 2, 2021

Related U.S. Application Data

(63) Continuation of application No. 16/642,974, filed as application No. PCT/KR2018/007515 on Jul. 3, 2018, now Pat. No. 11,103,436.

(30) Foreign Application Priority Data

Aug. 31, 2017 (KR) ........................ 10-2017-0111211

(51) Int. Cl.

| | | |
|---|---|---|
| *A61K 38/08* | (2019.01) | |
| *A61K 38/00* | (2006.01) | |
| *A61K 8/64* | (2006.01) | |
| *C07K 7/06* | (2006.01) | |
| *A61Q 19/02* | (2006.01) | |
| *A61Q 19/08* | (2006.01) | |
| *A61Q 19/00* | (2006.01) | |

(52) U.S. Cl.
CPC ................ *A61K 8/64* (2013.01); *A61K 38/08* (2013.01); *A61Q 19/02* (2013.01); *A61Q 19/08* (2013.01)

(58) Field of Classification Search
CPC .......... A61K 8/64; A61K 38/08; A61K 38/00; A61Q 19/02; A61Q 19/08; A61Q 19/00; C07K 7/06; C07K 5/1008
See application file for complete search history.

(56) References Cited

U.S. PATENT DOCUMENTS

| 5,516,891 | A | 5/1996 | Siwruk et al. |
|---|---|---|---|
| 8,343,501 | B2 | 1/2013 | Emanuel et al. |
| 8,344,211 | B2 | 1/2013 | Alexandrov et al. |
| 9,884,910 | B2 | 2/2018 | Fromond et al. |
| 10,047,125 | B2 | 8/2018 | Chung et al. |
| 10,676,507 | B2 | 6/2020 | Kim |
| 11,104,704 | B2 | 8/2021 | Chung et al. |
| 2008/0038838 | A1 | 2/2008 | Nakamura et al. |
| 2009/0012003 | A1 | 1/2009 | Ferrara et al. |
| 2011/0214205 | A1 | 9/2011 | Dietrich et al. |
| 2020/0197285 | A1 | 6/2020 | Chung et al. |

FOREIGN PATENT DOCUMENTS

| CN | 107001420 | A | 8/2017 |
|---|---|---|---|
| CN | 110461864 | A | 11/2019 |
| EP | 2754665 | A1 | 7/2014 |
| KR | 20110032587 | A | 3/2011 |
| KR | 10-1092915 | B1 | 12/2011 |
| KR | 20150029884 | A | 3/2015 |
| KR | 20170024469 | A | 3/2017 |
| WO | WO-2015/174601 | A1 | 11/2015 |
| WO | WO-2016/190660 | A1 | 12/2016 |
| WO | WO-2017/034301 | A1 | 3/2017 |

OTHER PUBLICATIONS

"Anti Wrinkle Test," Evalulab, <https://www.evalulab.com/en/clinical-testing/services/face-care/anti-wrinkle-test/>, retrieved Oct. 31, 2019 (2 pages).
"Anti-aging Cosmetic Reduced Wrinkles in Clinical Trial," The University of Manchester, <https://www.sciencedaily.com/releases/2009/04/090428093044.htm>, retrieved Oct. 31, 2019 (2009) (5 pages).
Das, "Psoriasis," Merck Manuals, <https://www.merckmanuals.com/home/skin-disorders/psoriasis-and-scaling-disorders/psoriasis?query=psoriasis>, retrieved Dec. 22, 2020, last modified Apr. 2020 (7 pages).
Dinulos, "Dry Skin (Xeroderma)," Merck Manuals, <https://www.merckmanuals.com/home/skin-disorders/cornification-disorders/dry-skin-xeroderma?query=xeroderma>, retrieved Dec. 22, 2020, last modified Nov. 2020 (2 pages).
Gonzalez, "Atopic Dermatitis (Eczema)," Merck Manuals <https://www.merckmanuals.com/home/skin-disorders/itching-and-dermatitis/atopic-dermatitis-eczema?query=atopic%20dermatitis>, retrieved Dec. 22, 2020, last modified Mar. 2018 (5 pages).
Gonzalez, "Contact Dermatitis," Merck Manuals, <https://www.merckmanuals.com/home/skin-disorders/itching-and-dermatitis/contact-dermatitis?query=non-allergic%20dermatitis>, retrieved Dec. 22, 2020, last modified Mar. 2018 (5 pages).
International Search Report, dated Feb. 19, 2019 for PCT International Application No. PCT/KR2018/007515, Chung et al., "Peptide Exhibiting Wrinkle-Improving Activity and Uses Thereof," filed Jul. 3, 2018 (6 pages).
Merrifield, "Solid Phase Peptide Synthesis. I. The Synthesis of a Tetrapeptide," J. Am. Chem. Soc. 85(14):2149-2154 (1963).
Partial Supplementary European Search Report dated May 3, 2021, for European Application No. 18850102.7, Chung et al., "Peptide Exhibiting Wrinkle-Improving Activity and Uses Thereof," filed Jul. 3, 2018 (11 pages).

(Continued)

*Primary Examiner* — Julie Ha
(74) *Attorney, Agent, or Firm* — Clark & Elbing LLP; Susan M. Michaud

(57) ABSTRACT

A peptide consisting of an amino acid sequence of SEQ ID NO: 1, 2, 3, or 4, a pharmaceutical composition for preventing or treating skin disease including the peptide, a cosmetic composition for skin condition improvement including the peptide, a food composition for skin condition improvement including the peptide, a method of preventing or treating skin disease using the peptide, and a use of the peptide in preventing or treating skin disease or improving skin condition are described.

12 Claims, 32 Drawing Sheets

Specification includes a Sequence Listing.

(56) References Cited

OTHER PUBLICATIONS

Wells, "Basal Cell Carcinoma," Merck Manuals, <https://www.merckmanuals.com/home/skin-disorders/skin-cancers/basal-cell-carcinoma>, retrieved Dec. 22, 2020, last modified May 2019 (3 pages).
Wells, "Melanoma," Merck Manuals, <https://www.merckmanuals.com/home/skin-disorders/skin-cancers/melanoma?query=melanoma>, retrieved Dec. 22, 2020, last modified May 2019 (7 pages).
Wells, "Overview of Skin Cancer," Merck Manuals, <https://www.merckmanuals.com/home/skin-disorders/skin-cancers/overview-of-skin-cancer?query=skin%20disease>, retrieved Dec. 22, 2020, last modified May 2019 (2 pages).
Wells, "Squamous Cell Carcinoma," Merck Manuals, <https://www.merckmanuals.com/home/skin-disorders/skin-cancers/squamous-cell-carcinoma>, retrieved Dec. 22, 2020, last modified May 2019 (3 pages).
"Wrinkles —Diagnosis and Treatment," The Mayo Clinic, <https://www.mayoclinic.org/diseases-conditions/wrinkles/diagnosis-treatment/drc-20354931>, retrieved Oct. 31, 2019 (7 pages).
Extended European Search Report for European Patent Application No. 18850102.7, applicant Caregen Co., Ltd., dated Sep. 3, 2021 (16 pages).

PEPTIDE EXHIBITING WRINKLE-IMPROVING ACTIVITY AND USES THEREOF

SEQUENCE LISTING

The instant application contains a Sequence Listing which has been submitted electronically in ASCII format and is hereby incorporated by reference in its entirety. Said ASCII copy, created on Jul. 14, 2021 is named 51401-028002_Sequence_Listing_7.14.21_ST25 and is 3,359 bytes in size.

TECHNICAL FIELD

The present disclosure relates to a peptide consisting of an amino acid sequence of SEQ ID NO: 1, 2, 3, or 4, a pharmaceutical composition for preventing or treating skin disease including the peptide, a cosmetic composition for skin condition improvement including the peptide, a food composition for skin condition improvement including the peptide, a method of preventing or treating skin disease using the peptide, and a use of the peptide in preventing or treating skin disease or improving skin condition.

BACKGROUND ART

Human skin constantly changes, the most representative of which is deterioration of skin function and decrease of visual beauty due to aging. Skin aging is classified into endogenous aging due to genetic factors and exogenous aging due to external environmental factors such as sunlight.

Wrinkles are formed on the skin due to aging, and representative wrinkle formation factors include active oxygen, ultraviolet rays, and decrease in collagen biosynthesis. In the case of endogenous aging of the skin, artificial control is not possible, but in the case of exogenous aging, aging may be prevented, treated, or delayed by removing active oxygen, proliferating fibroblasts, and promoting collagen biosynthesis.

DESCRIPTION OF EMBODIMENTS

Technical Problem

The present inventors have endeavored to develop an excellent peptide having biologically effective activity. As a result, it was found that a peptide including an amino acid sequence of SEQ ID NO: 1, 2, 3, or 4 may be effectively used in improving skin wrinkle, thereby completing the present disclosure.

An object of the present disclosure is to provide a peptide consisting of an amino acid sequence of SEQ ID NO: 1, 2, 3, or 4.

Another object of the present disclosure is to provide a pharmaceutical composition for preventing or treating skin disease including at least one peptide selected from the group consisting of a peptide consisting of an amino acid sequence of SEQ ID NO: 1 or 2.

Still another object of the present disclosure is to provide a cosmetic composition for skin condition improvement including at least one peptide selected from the group consisting of a peptide consisting of an amino acid sequence of SEQ ID NO: 1, 2, 3, or 4.

Still another object of the present disclosure is to provide a food composition for skin condition improvement including at least one peptide selected from the group consisting of a peptide consisting of an amino acid sequence of SEQ ID NO: 1, 2, 3, or 4.

Still another object of the present disclosure is to provide a method of preventing or treating skin disease using a peptide consisting of an amino acid sequence of SEQ ID NO: 1 or 2.

Still another object of the present disclosure is to provide a use of a peptide consisting of an amino acid sequence of SEQ ID NO: 1, 2, 3, or 4 in improving skin condition.

Still another object of the present disclosure is to provide a use of a peptide consisting of an amino acid sequence of SEQ ID NO: 1 or 2 in preventing or treating skin disease.

Solution to Problem

The present disclosure relates to a peptide consisting of an amino acid sequence of SEQ ID NO: 1, 2, 3, or 4, a pharmaceutical composition for preventing or treating skin disease including the peptide, a cosmetic composition for skin condition improvement including the peptide, a food composition for skin condition improvement including the peptide, a method of preventing or treating skin disease using the peptide, and a use of the peptide in preventing or treating skin disease or improving skin condition.

Representative features of a skin wrinkle area are decreased level of extracellular matrix proteins (ECM), such as collagen, elastin, and fibronectin levels, which constitute dermis.

In order to exhibit the effect of improving skin wrinkles, it is necessary to show the effect of increasing the expression of ECM molecules by promoting proliferation and activation of fibroblasts, which are the main cells constituting the dermis. In order to confirm the efficacy of these peptides, MTT assay, MAPK, AKT phosphorylation level test (phosphorylation form is the active form of signaling molecules associated with cell proliferation), collagen, elastin, and fibronectin expression test (identification of mRNA levels by RT-PCR and protein levels by ELISA) were carried out. As a result, positive effects were shown.

In addition, by observing the effect of promoting the proliferation of keratinocytes, which are epidermal constituent cells, and increasing the expression of HA, AQP3, and SIRT1, it was confirmed that the peptide has an effect of inhibiting external stimulation by barrier strengthening.

Hereinafter, the present disclosure will be described in further detail.

An aspect of the present disclosure relates to a peptide consisting of an amino acid sequence of SEQ ID NO: 1, 2, 3, or 4.

In the peptide, an N-terminal and/or C-terminal modification may be induced to select a portion of the amino acid sequence and increase its activity. Such N-terminal and/or C-terminal modification may significantly improve stability of the peptide of the present disclosure. For example, the half-life in vivo administration of the peptide may be increased.

The N-terminal of the peptide may be modified by being linked to a protecting group selected from the group consisting of an acetyl group, a fluorenylmethoxycarbonyl group, a formyl group, a palmitoyl group, a myristyl group, a stearyl group, and a polyethylene glycol (PEG).

The C-terminal of the peptide may be modified by being linked to a hydroxyl group (—OH), an amino group (—NH$_2$), an azide group (—NHNH$_2$), or the like, but is not limited thereto.

The protecting group acts to protect the peptide of the present invention against attack of a protein cleavage enzyme in vivo.

An aspect of the present disclosure relates to a pharmaceutical composition for preventing or treating skin disease including at least one peptide selected from the group consisting of a peptide consisting of an amino acid sequence of SEQ ID NO: 1 or 2.

The skin disease may be psoriasis, atopic dermatitis, non-allergic dermatitis, and xeroderma, but is not limited thereto.

The pharmaceutical composition may comprise a pharmaceutically effective amount of at least one peptide selected from the group consisting of a peptide consisting of an amino acid sequence of SEQ ID NO: 1 or 2.

In addition, the pharmaceutical composition may further include a pharmaceutically acceptable carrier.

The pharmaceutically acceptable carrier may be any suitable carrier generally included in preparation. The pharmaceutically acceptable carrier may include lactose, dextrose, sucrose, sorbitol, mannitol, starch, acacia rubber, calcium phosphate, alginate, gelatin, calcium silicate, microcrystalline cellulose, polyvinylpyrrolidone, cellulose, water, syrup, methyl cellulose, methylhydroxybenzoate, propylhydroxybenzoate, talc, magnesium stearate, and mineral oil, but is not limited thereto. The pharmaceutically acceptable carrier and preparation that are suitable for use are described in detail in Remington's Pharmaceutical Sciences (19th ed., 1995).

The pharmaceutical composition may further include, in addition to the foregoing ingredients, a lubricant, a humectant, a sweetener, a flavoring agent, an emulsifier, a suspension, or a preservative, but is not limited thereto.

The pharmaceutical composition may be orally or parenterally administered. Preferably, the pharmaceutical composition may be parenterally administered. Parental administration may be intramuscular administration, intravenous administration, subcutaneous administration, intraperitoneal administration, local administration, or dermal administration, but is not limited thereto.

The dosage of the pharmaceutical composition may be in a range of 0.0001 microgram (μg) to 1,000 μg (0.001 μg to 1,000 μg, 0.01 μg to 1,000 μg, 0.1 μg to 1,000 μg, or 1.0 μg to 1,000 μg) per day, but is not limited thereto. Prescription may vary depending on the preparation method, administration method, age, weight, sex, pathological condition, food, administration time, administration route, excretion rate, and responsiveness of the patient.

The pharmaceutical composition may be prepared in a form of a unit dose by formulating it with a pharmaceutically acceptable carrier and/or excipient or prepared in a multi-dose container according to a method which may be easily carried out by one of ordinary skill in the art to which the present invention belongs.

The formulation may be in a form of solutions, suspensions, or emulsions in oils or aqueous media or in a form of excipients, powders, granules, tablets, or capsules, and may additionally contain dispersing agents and/or stabilizers.

Still another aspect of the present disclosure relates to a food composition for skin condition improvement including as an active ingredient at least one peptide selected from the group consisting of a peptide consisting of an amino acid sequence of SEQ ID NO: 1, 2, 3, or 4

The skin condition improvement may be wrinkle improvement, skin regeneration, skin elasticity improvement, skin aging inhibition, wound regeneration, acne improvement, skin regeneration, or skin whitening, but is not limited thereto.

The food may be various foods, beverages, food additives, and the like.

An amount of the peptide as an active ingredient contained in the food composition is not particularly limited and may be properly controlled depending on a type of food or a desired used thereof. For example, an amount of the peptide may be added in a range of 0.01% to 15% by weight of the total food weight, and an amount of the peptide may be added to a health beverage composition in a range of 0.02 g to 10 g, preferably 0.3 g to 1 g based on 100 mL.

When the food is a beverage, liquid components are not particularly limited except that the peptide is contained as an essential ingredient in the indicated ratio, and the beverage may contain additional ingredients such as various flavoring agents or natural carbohydrates as in general beverages.

Examples of the natural carbohydrates include conventional sugars, such as monosaccharides, e.g., glucose, fructose, and the like; disaccharides, e.g., maltose, sucrose, and the like; and polysaccharides, e.g., dextrin, cyclodextrin, and sugar alcohols such as xylitol, sorbitol, and erythritol.

As a flavoring agent other than the above-mentioned, a natural flavoring agent (taumartin or a *stevia* extract, e.g., rebaudioside A, glycyrrhizin, or the like); and a synthetic flavoring agent such as saccharin, aspartame. and the like may be used. A ratio of such natural carbohydrates may be generally about 1 g to 20 g, preferably 5 g to 12 g per 100 mL of the composition of the present disclosure.

In addition to the above, the food composition of the present disclosure may contain various nutrients, vitamins, minerals (electrolytes), flavors such as synthetic and natural flavors, coloring agents and neutralizing agents (cheese, chocolate, etc.), pectic acid and salts thereof, alginic acid and salts thereof, organic acids, protective colloidal thickeners, pH adjusters, stabilizers, preservatives, glycerin, alcohols, carbonation agents used in carbonated beverages, and the like.

In addition, the food composition of the present disclosure may contain flesh for the production of natural fruit juices, fruit juice drinks, and vegetable drinks. These components may be used independently or in combination. A ratio of such additives is not critical but is generally in a range of 0 to about 20 parts by weight per 100 parts by weight of the composition of the present disclosure.

Still another aspect of the present disclosure relates to a cosmetic composition for skin condition improvement including at least one selected from the group consisting of a peptide consisting of an amino acid sequence of SEQ ID NO: 1, 2, 3, or 4.

The skin condition improvement may be wrinkle improvement, skin regeneration, skin elasticity improvement, skin aging inhibition, wound regeneration, acne improvement, skin regeneration, or skin whitening, but is not limited thereto.

The cosmetic composition may include: (a) a cosmetically effective amount of the peptide of the present disclosure and/or (b) a cosmetically acceptable carrier, but is not limited thereto.

The term "cosmetic effective amount" as used herein means an amount sufficient to achieve the skin improving efficacy of the composition of the present disclosure described above.

The cosmetic composition may be prepared in any formulation conventionally prepared in the art, for example, solutions, suspensions, emulsions, pastes, gels, creams, lotions, powders, soaps, surfactant-containing cleansing, oils, powder foundations, emulsion foundations, wax foundations, sprays, and the like, but is not limited thereto. More specifically, the cosmetic composition may be prepared in the form of a flexible lotion, nutrition lotion, nutrition cream, massage cream, essence, eye cream, cleansing cream, cleansing foam, cleansing water, pack, spray, or powder.

When a formulation of a cosmetic product of the present disclosure is a paste, cream, or gel, animal oils, vegetable oils, waxes, paraffins, starches, trachants, cellulose derivatives, polyethylene glycols, silicones, bentonites, silicas, talc or zinc oxide may be used as a carrier component.

When a formulation of a cosmetic product of the present disclosure is powder or spray, lactose, talc, silica, aluminum hydroxide, calcium silicate, or polyamide powder may be used as a carrier component. In particular, in the case of spray, a propellant such as chlorofluorohydrocarbon, propane/butane, or dimethyl ether may be further included.

When a formulation of a cosmetic product of the present disclosure is a solution or emulsion, a solvent, a solubilizer, or an emulsifier is used as a carrier component, such as water, ethanol, isopropanol, ethyl carbonate, ethyl acetate, benzyl alcohol, benzyl benzoate, propylene glycol, 1,3-butylglycol oil, glycerol aliphatic ester, polyethylene glycol, or fatty acid esters of sorbitan.

When a formulation of a cosmetic product of the present disclosure is a suspension, a liquid diluent such as water, ethanol, or propylene glycol, a suspending agent such as ethoxylated isostearyl alcohol, polyoxyethylene sorbitol ester, and polyoxyethylene sorbitan ester, microcrystalline cellulose, aluminum metahydroxide, bentonite, agar, or tracant may be used as a carrier component.

When a formulation of a cosmetic product of the present disclosure is a surfactant-containing cleansing, as a carrier component, aliphatic alcohol sulfate, aliphatic alcohol ether sulfate, sulfosuccinic acid monoester, isethionate, an imidazolinium derivative, methyltaurate, sarcosinate, fatty acid amide ether sulfate, alkylamidobetaine, aliphatic alcohol, fatty acid glyceride, fatty acid diethanolamide, vegetable oil, a lanolin derivative, or ethoxylated glycerol fatty acid ester may be used.

Components included in the cosmetic composition of the present disclosure include components conventionally used in cosmetic compositions, in addition to a peptide and a carrier component as active ingredients, for example, conventional adjuvants such as antioxidants, stabilizers, solubilizers, vitamins, pigments, and flavorings.

The term "skin condition improvement" as used herein encompasses a process of treating, alleviating, or relieving damage to skin caused by intrinsic or extrinsic factors of the skin or its effect. For example, the term may mean alleviating or improving inflammation in skin, but it is not limited thereto.

Still another aspect of the present disclosure relates to a use of a peptide consisting of an amino acid sequence of SEQ ID NO: 1, 2, 3, or 4 in improving skin condition.

The skin condition improvement may be wrinkle improvement, skin regeneration, skin elasticity improvement, skin aging inhibition, wound regeneration, acne improvement, skin regeneration, or skin whitening, but is not limited thereto.

Still another aspect of the present disclosure relates to a use of a peptide consisting of an amino acid sequence of SEQ ID NO: 1 or 2 in preventing or treating skin disease.

The skin disease may be psoriasis, atopic dermatitis, non-allergic dermatitis, and xeroderma, but is not limited thereto.

The peptide consisting of an amino acid sequence of SEQ ID NO: 1 or 2 is the same as those described above.

The term "peptide" as used herein refers to a linear molecule formed by binding amino acid residues to each other by peptide bonds. The peptides of the present disclosure may be prepared by chemical synthesis methods known in the art, in particular solid-phase synthesis techniques (solid-phase synthesis techniques; Merrifield, J. Amer. Chem. Soc. 85:2149-54(1963); Stewart, et al., Solid Phase Peptide Synthesis, 2nd. ed., Pierce Chem. Co.: Rockford, 111(1984)) or liquid phase synthesis technology (U.S. Pat. No. 5,516,891).

The term "stability" as used herein means not only in vivo stability but also storage stability (e.g., room temperature storage stability).

The term "pharmaceutically effective amount" as used herein means an amount sufficient to achieve the efficacy or activity of the peptides described above.

Advantageous Effects of Disclosure

The present disclosure relates to a peptide consisting of an amino acid sequence of SEQ ID NO: 1, 2, 3, or 4, a pharmaceutical composition for preventing or treating skin disease including the peptide, a cosmetic composition for skin condition improvement including the peptide, a food composition for skin condition improvement including the peptide, a method of preventing or treating skin disease using the peptide, and a use of the peptide in preventing or treating skin disease or improving skin condition.

BEST MODE

Figure 1:
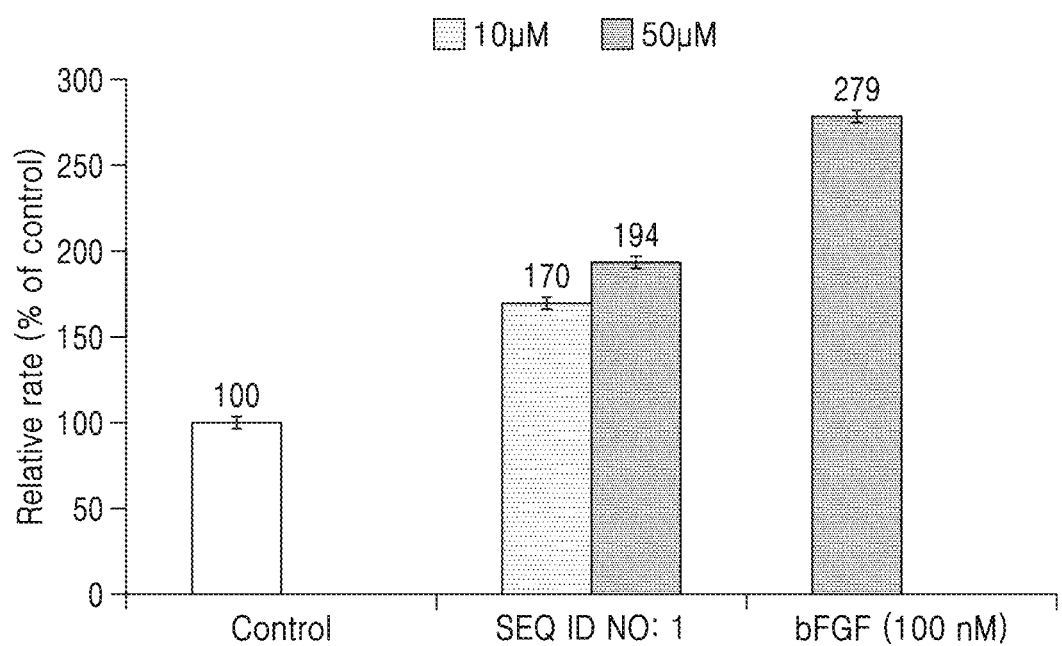
FIG. 1 is a graph showing evaluation results of proliferation of fibroblasts of a peptide consisting of an amino acid sequence of SEQ ID NO: 1 according to an embodiment the present disclosure.

The present disclosure relates to a peptide consisting of an amino acid sequence of SEQ ID NO: 1, 2, 3, or 4.

MODE OF DISCLOSURE

Hereinafter, the present invention will be described in further detail with reference to Examples. However, these Examples are for illustrative purposes only, and the present disclosure is not intended to be limited by these Examples.

Synthesis Example 1: Synthesis of Peptide 70 g of chlorotrityl chloride resin (CTC resin, Nova biochem Cat No. 01-64-0021) was placed in a reaction vessel, and 490 mL of methylene chloride (MC) was added thereto and stirred for 3 minutes. Then, the solution was removed, 490 mL of dimethylformamide (DMF) was added thereto, the mixture was stirred for 3 minutes, and then the solvent was removed. 700 mL of dichloromethane solution was added to the reactor, and 200 mmole of Fmoc-Tyr (tBu)-OH (Bachem, Switzerland) and 400 mmole of diisopropylethylamine (DIEA) were added thereto followed by stirring and dissolving. The reaction was carried out with stirring for 1 hour. After washing, methanol and DIEA (2:1) were dissolved in dechloromethane (DCM), reacted for 10 minutes, and washed with excess DCM/DMF (1:1). Then, the solution was removed, 490 mL of dimethylformamide (DMF) was added thereto, the mixture was stirred for 3 minutes, and then the solvent was removed. 700 mL of a deprotection solution (20% piperidine/DMF) was added to the reaction vessel, stirred at room temperature for 10 minutes, and then the solution was removed. The same amount of a deprotection solution was added thereto, and the reaction was maintained for 10 minutes. The solution was then removed and washed three minutes each twice with DMF, once with MC, and once with DMF to thereby prepare Tyr(tBu)-CTC resin.

700 mL of a DMF solution was added to another reactor, and 200 mmole of Fmoc-Arg (Pbf)-OH (Bachem, Switzerland), 200 mmole of HoBt, and 200 mmole of HBTu were added thereto, followed by dissolving with stirring. The reactor was charged with 400 mmole DIEA in two portions and stirred for at least 5 minutes until all the solids dissolved. The dissolved amino acid mixture solution was placed in a reaction vessel containing the deprotected resin and allowed to react for 1 hour at room temperature with stirring. The reaction solution was removed, and the mixture was stirred with DMF solution three times for 5 minutes and then removed. A small amount of the reaction resin was taken, and the degree of reaction was checked using a Kaiser test (Nihydrin Test). Arg(Pbf)-Tyr(tBu)-CTC resin was prepared by the same deprotection reaction twice as described above using the deprotection solution. After thoroughly washing with DMF and MC and once again performing a Kaiser test, the following amino acid adhesion experiment was performed as described above. Fmoc-Gly-OH, Fmoc-Gly-OH, Fmoc-Gly-OH, Fmoc-Trp-OH, Fmoc-Lys(Boc)-OH were sequenced according to the selected amino acid sequence. The Fmoc-protecting group was reacted twice with the deprotecting solution for 10 minutes, followed by washing for removing the solution. Peptidyl resin was washed three times each with DMF, MC and methanol, dried slowly by flowing nitrogen air, and then completely dried by vacuum under reduced pressure in $P_2O_5$, followed by addition of 1,900 mL of a deodorant solution (trifluroacetic acid 81.5%, distilled water 5.0%, thioanisole 5.0%, phenol 5.0%, ethanedithiol (EDT) 2.5%, and triisopropylsilane (TIS) 1.0%). The mixture was then shaken at room temperature, and the reaction was maintained for 2 hours. The resin was filtered, and the resin was washed with a small amount of TFA solution and then combined with the mother liquid. 2,090 mL of the combined mother liquid was added with cold ether to induce precipitation, and the precipitate was collected by centrifugation and washed twice with cold ether. The mother liquid was removed and sufficiently dried under nitrogen to synthesize 79.8 g of the peptide consisting of SEQ ID NO: 1 before purification (yield: 97.0%). The molecular weight was 822.9 (theoretical value: 822.9) when the molecular weight was measured using a molecular weight analyzer.

The peptide consisting of an amino acid sequence of SEQ ID NO: 2, SEQ ID NO: 3, or SEQ ID NO: 4 was synthesized in the same manner as described above.

TABLE 1

| SEQ ID NO. | Sequence listing | Analysis value (mass analyzer) | |
|---|---|---|---|
| | | Analytical value | Theoretical value |
| 1 | KWGGGRY | 822.9 | 822.9 |
| 2 | ILGRWCG | 803.9 | 803.9 |
| 3 | GPVH | 408.4 | 408.4 |
| 4 | EDEFKPPAAGR | 1216.3 | 1216.3 |

Example 1. Assessment of Promotion of Proliferation of Fibroblasts

Mouse fibroblast NIH3T3 was seeded in a 96-well plate at a density of $5 \times 10^3$ cells/well, and then cultured overnight. Subsequently, the media were changed to 0.05% serum-containing media. Then, treatment with the positive control, i.e., 100 nM bFGF, and 10 μM or 50 μM of the peptide consisting of an amino acid sequence of SEQ ID NO: 1, 2, 3, or 4 were performed and cultured for 3 days. Then, 4 mg/mL MTT solution treatment was performed, and the reaction was carried out for 4 hours. Then, the resulting formazan was dissolved by treatment with dimethyl sulfoxide (hereinafter referred to as "DMSO"), and the absorbance at 560 nm was measured using a microplate reader. The results are shown in FIGS. 1 to 4 and Table 2.

TABLE 2

Figure 2:
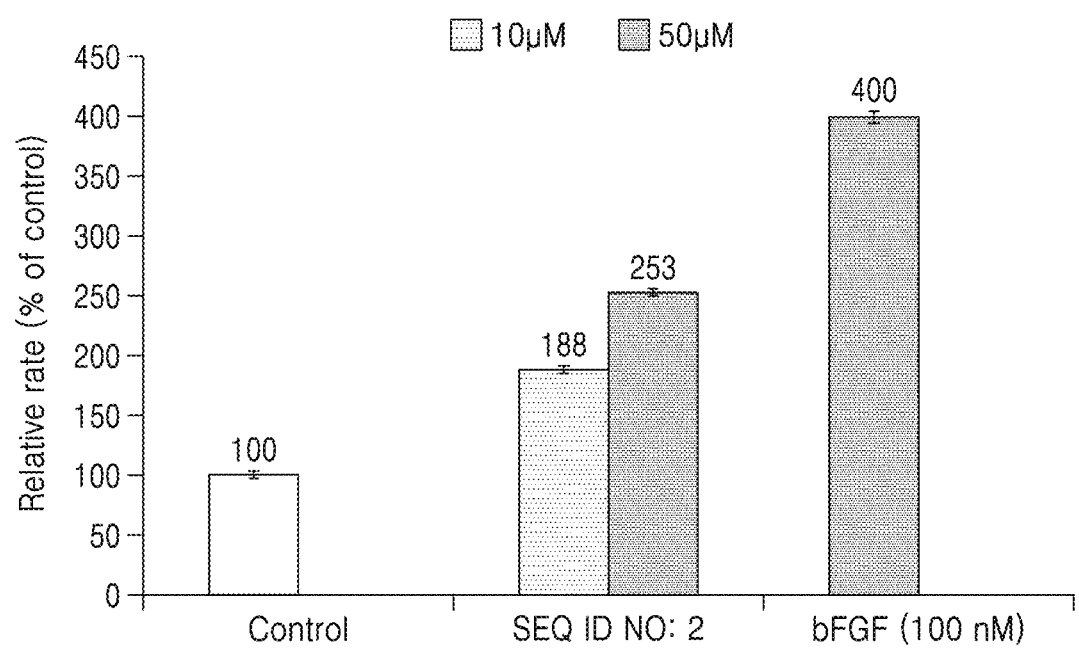
FIG. 2 is a graph showing evaluation results of proliferation of fibroblasts of a peptide consisting of an amino acid sequence of SEQ ID NO: 2 according to an embodiment the present disclosure.
Figure 3:
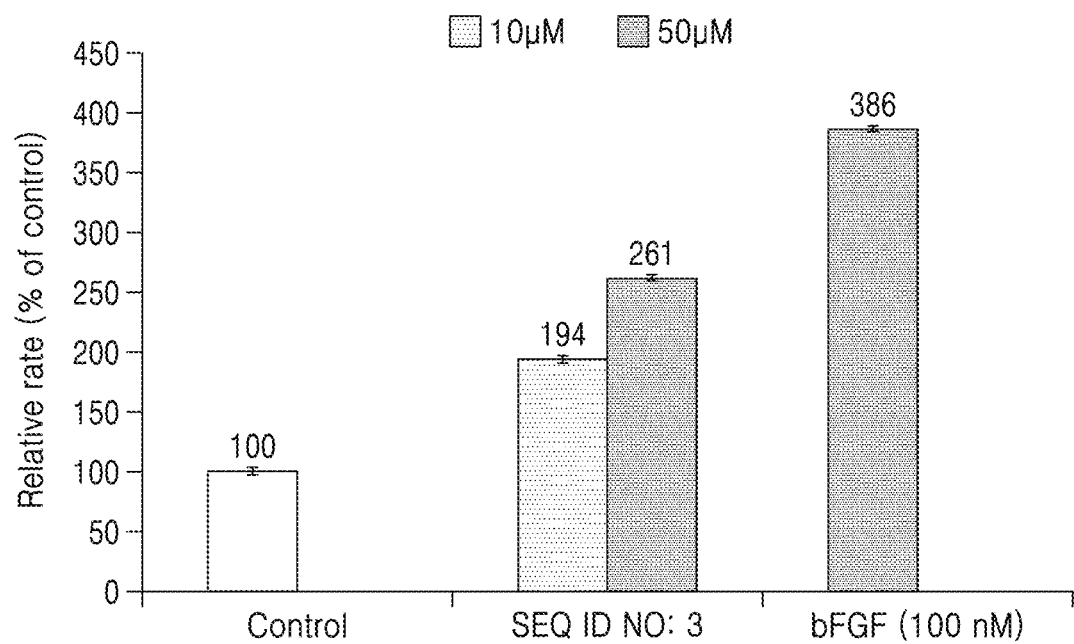
FIG. 3 is a graph showing evaluation results of proliferation of fibroblasts of a peptide consisting of an amino acid sequence of SEQ ID NO: 3 according to an embodiment the present disclosure.
Figure 4:
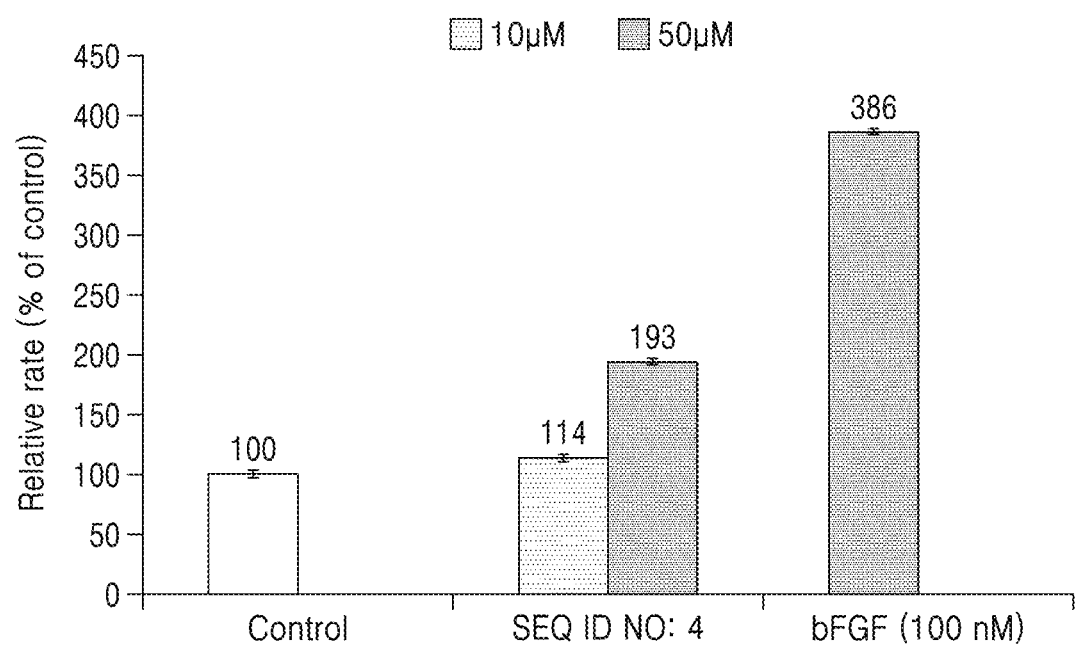
FIG. 4 is a graph showing evaluation results of proliferation of fibroblasts of a peptide consisting of an amino acid sequence of SEQ ID NO: 4 according to an embodiment the present disclosure.

| | | Fibroblast proliferation (%) | | |
|---|---|---|---|---|
| FIG. 1 | Control | SEQ ID NO: 1 | | bFGF |
| | | 10 μM | 50 μM | (100 nM) |
| | 100 | 170 | 194 | 279 |
| FIG. 2 | Control | SEQ ID NO: 2 | | bFGF |
| | | 10 μM | 50 μM | (100 nM) |
| | 100 | 188 | 253 | 400 |
| FIG. 3 | Control | SEQ ID NO: 3 | | bFGF |
| | | 10 μM | 50 μM | (100 nM) |
| | 100 | 194 | 261 | 386 |
| FIG. 4 | Control | SEQ ID NO: 4 | | bFGF |
| | | 10 μM | 50 μM | (100 nM) |
| | 100 | 114 | 193 | 386 |

As shown in FIGS. 1 to 4 and Table 2, the peptide consisting of an amino acid sequence of SEQ ID NO: 1, SEQ ID NO: 2, SEQ ID NO: 3, or SEQ ID NO: 4 was found to promote fibroblast proliferation.

Example 2. Assessment of Promotion of Proliferation of Keratinocytes

Human keratinocyte HaCaT was seeded in a 6-well plate at a density of $3 \times 10^5$ cells/well, and then cultured overnight. Subsequently, the media were changed to 0.05% serum-containing media. Then, treatment with the positive control, i.e., 10 nM EGF, and 10 μM or 50 μM of the peptide consisting of an amino acid sequence of SEQ ID NO: 1, 2, 3, or 4 were performed and cultured for 3 days. Then, 4 mg/mL MTT solution treatment was performed, and the reaction was carried out for 4 hours. Then, the resulting formazan was dissolved by treatment with dimethyl sulfoxide (hereinafter referred to as "DMSO"), and the absorbance at 560 nm was measured using a microplate reader. The results are shown in FIGS. 5 to 8 and Table 3.

TABLE 3

Figure 5:
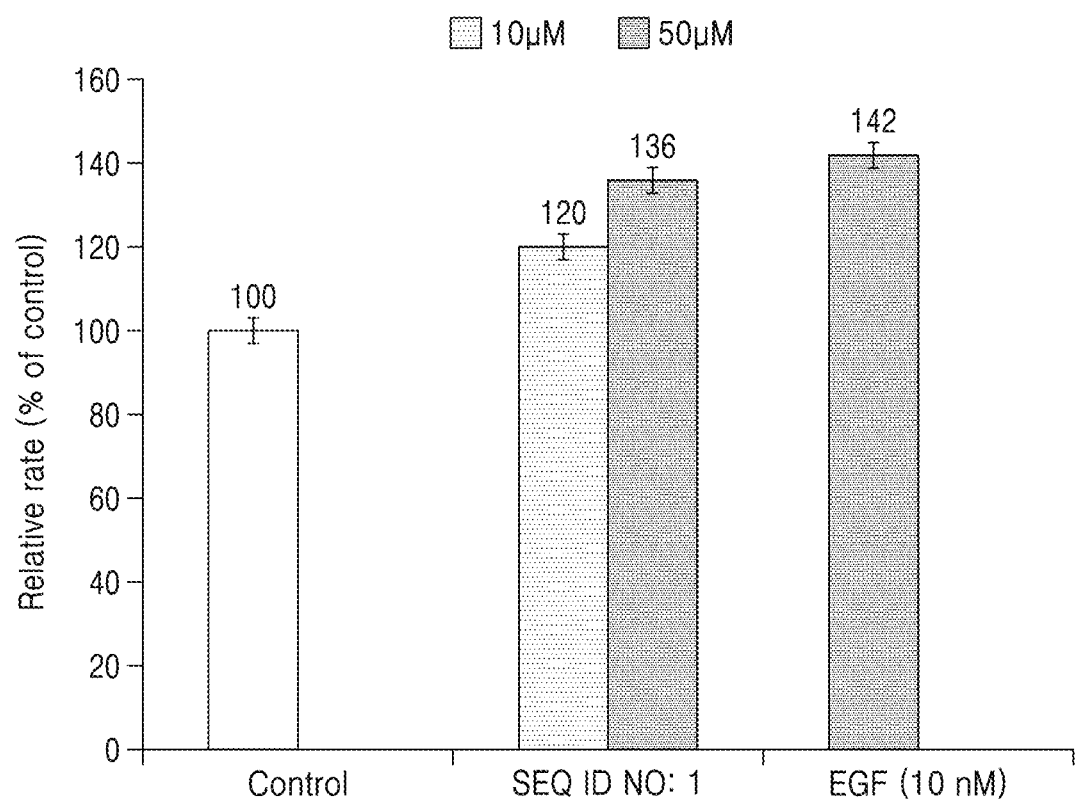
FIG. 5 is a graph showing evaluation results of proliferation of keratinocytes of a peptide consisting of an amino acid sequence of SEQ ID NO: 1 according to an embodiment the present disclosure.
Figure 6:
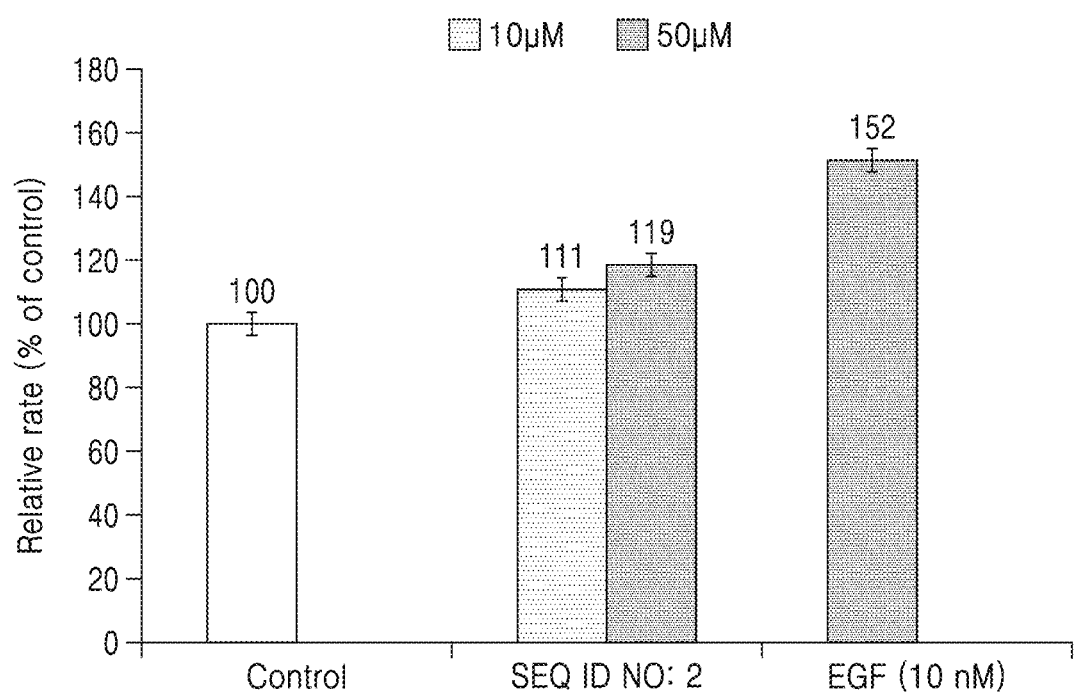
FIG. 6 is a graph showing evaluation results of proliferation of keratinocytes of a peptide consisting of an amino acid sequence of SEQ ID NO: 2 according to an embodiment the present disclosure.
Figure 7:
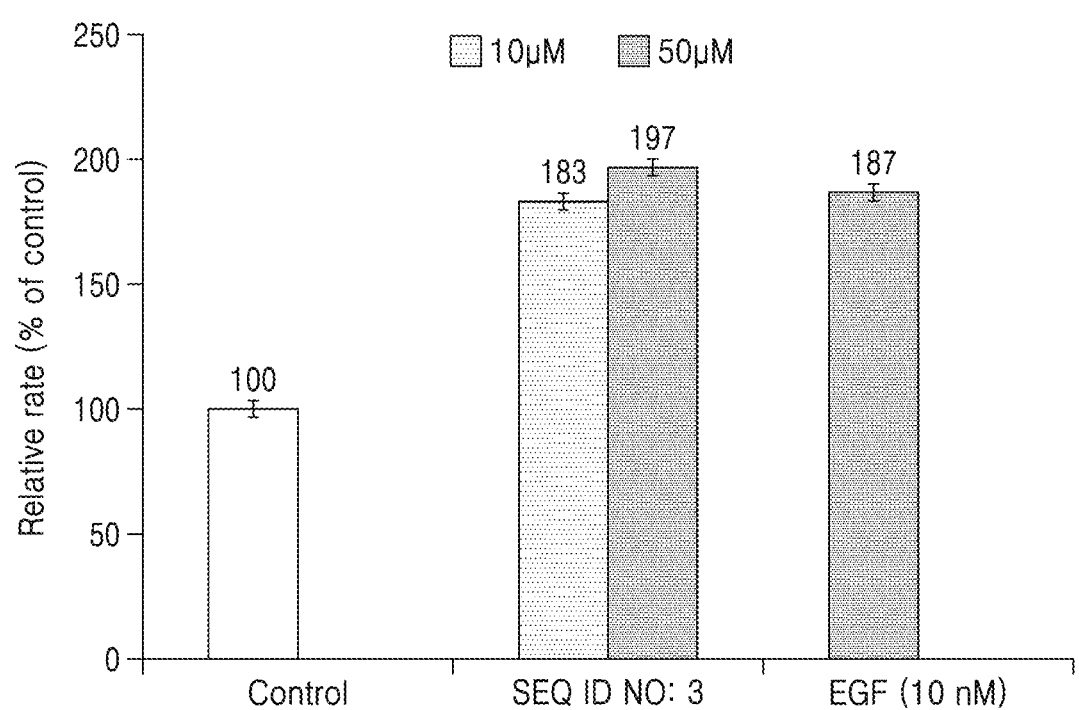
FIG. 7 is a graph showing evaluation results of proliferation of keratinocytes of a peptide consisting of an amino acid sequence of SEQ ID NO: 3 according to an embodiment the present disclosure.

| | | Keratinocyte proliferation (%) | | |
|---|---|---|---|---|
| FIG. 5 | Control | SEQ ID NO: 1 | | EGF |
| | | 10 μM | 50 μM | (10 nM) |
| | 100 | 120 | 136 | 142 |
| FIG. 6 | Control | SEQ ID NO: 2 | | EGF |
| | | 10 μM | 50 μM | (10 nM) |
| | 100 | 111 | 119 | 152 |
| FIG. 7 | Control | SEQ ID NO: 3 | | EGF |
| | | 10 μM | 50 μM | (10 nM) |
| | 100 | 183 | 197 | 187 |

TABLE 3-continued

Figure 8:
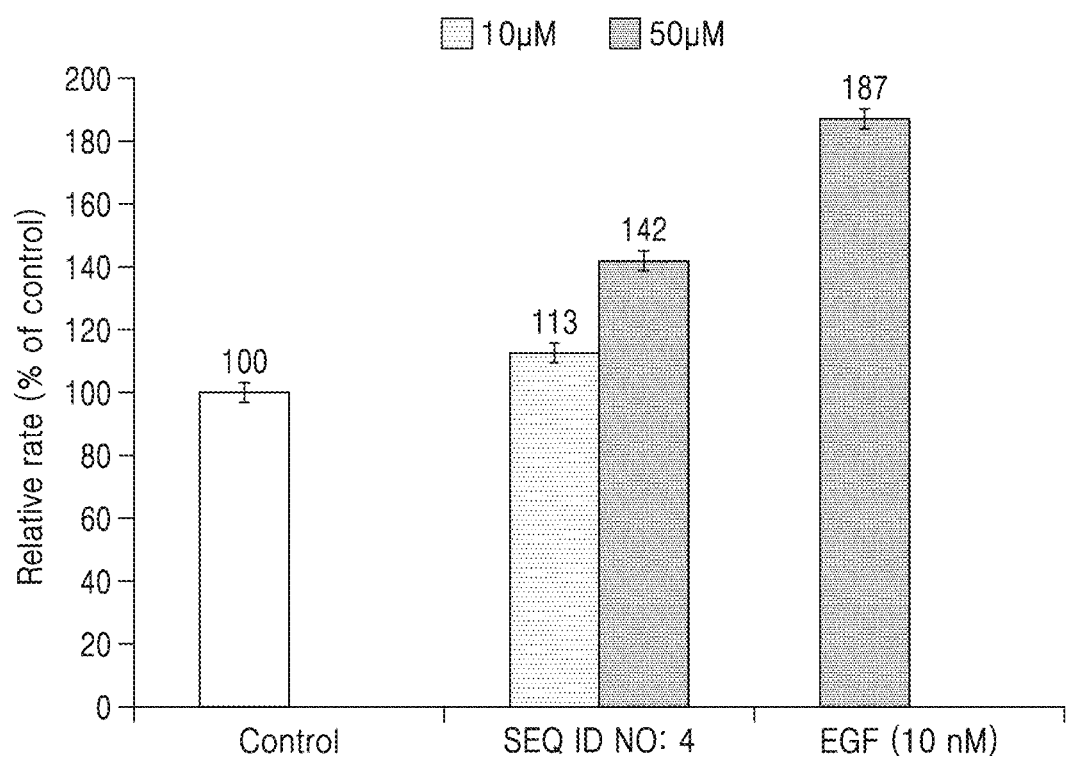
FIG. 8 is a graph showing evaluation results of proliferation of keratinocytes of a peptide consisting of an amino acid sequence of SEQ ID NO: 4 according to an embodiment the present disclosure.
Figure 9:
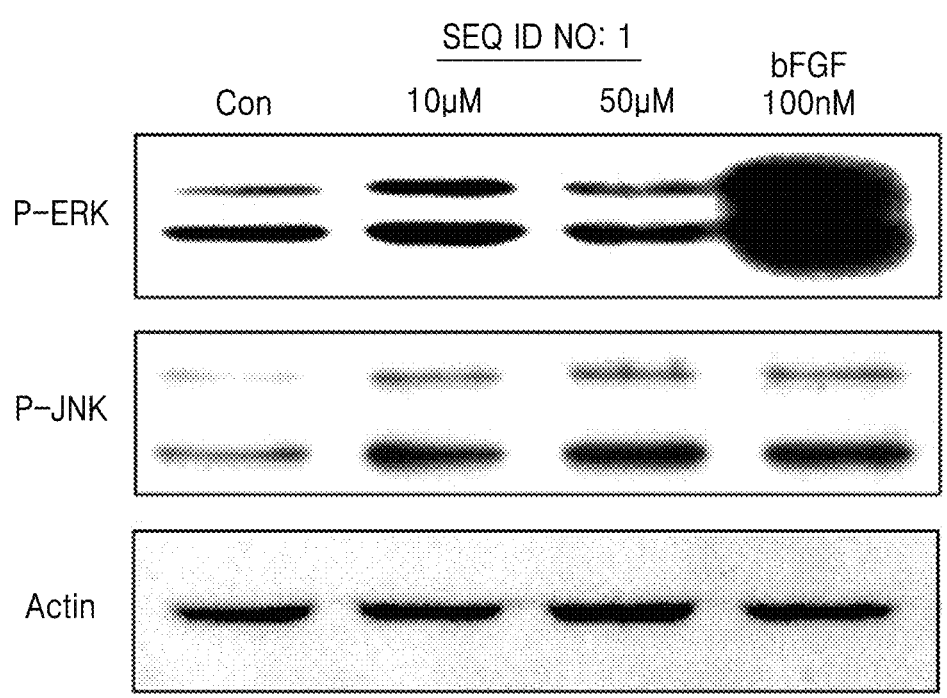
FIG. 9 is an image showing measurement results of phosphorylation level of MAPK (AKT elimination) in fibroblasts of a peptide consisting of an amino acid sequence of SEQ ID NO: 1 according to an embodiment the present disclosure.
Figure 10:
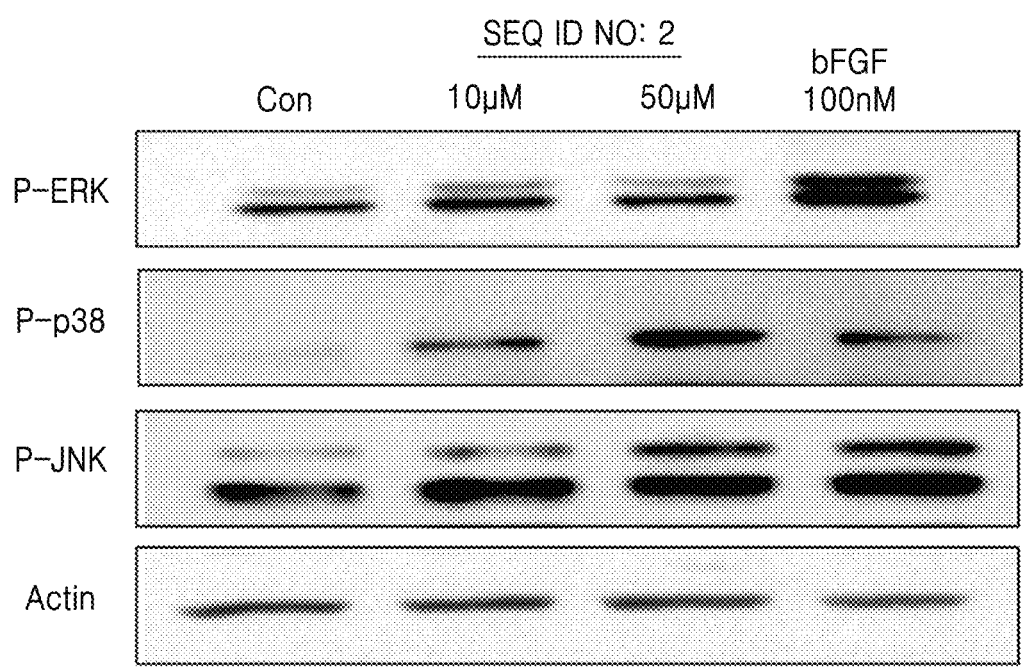
FIG. 10 is an image showing measurement results of phosphorylation level of MAPK (AKT elimination) in fibroblasts of a peptide consisting of an amino acid sequence of SEQ ID NO: 2 according to an embodiment the present disclosure.
Figure 11:
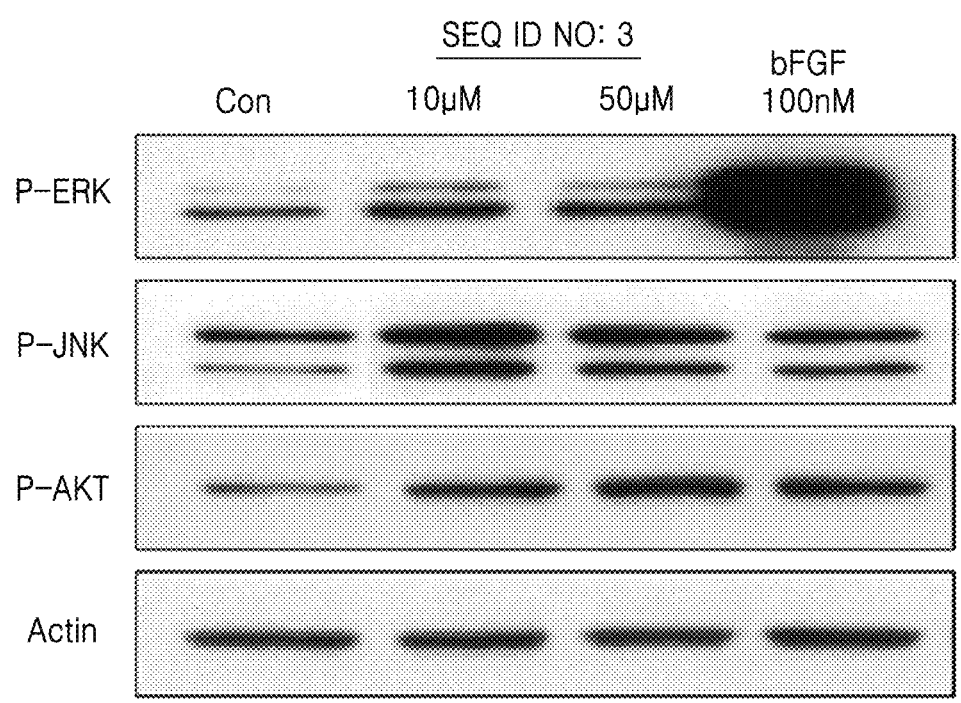
FIG. 11 is an image showing measurement results of phosphorylation level of MAPK and AKT in fibroblasts of a peptide consisting of an amino acid sequence of SEQ ID NO: 3 according to an embodiment the present disclosure.
Figure 12:
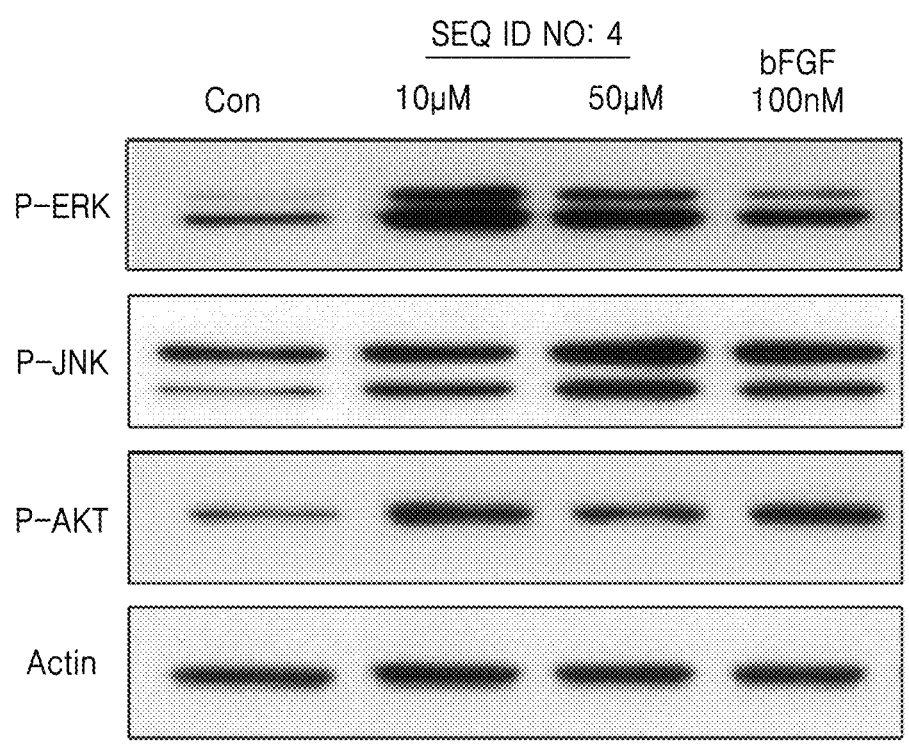
FIG. 12 is an image showing measurement results of phosphorylation level of MAPK and AKT in fibroblasts of a peptide consisting of an amino acid sequence of SEQ ID NO: 4 according to an embodiment the present disclosure.

| | Keratinocyte proliferation (%) | | | |
|---|---|---|---|---|
| FIG. 8 | Control | SEQ ID NO: 4 | | EGF |
| | | 10 μM | 50 μM | (10 nM) |
| | 100 | 113 | 142 | 187 |

Example 3. Measurement of Phosphorylation Level of MAPK and AKT 3-1. Fibroblasts Mouse fibroblast NIH3T3 was seeded in a 6-well plate at a density of $5 \times 10^3$ cells/well, and then cultured overnight. Subsequently, the media were changed to 0.05% FBS-containing media. Then, treatment with the positive control, i.e., 100 nM bFGF, and 10 μM or 50 μM of the peptide consisting of an amino acid sequence of SEQ ID NO: 1, 2, 3, or 4 were performed and cultured for 30 minutes. Then, the cells were collected to prepare cell lysate. Then, western blotting was performed using P-MAPK (p-Erk, p-JNK, p-p38) and p-Akt or actin antibody (Santacruz Biotechnology, USA). The comparison results of phosphorylation aspects thereof are shown in FIGS. 9 to 12.

As shown in FIGS. 9 to 12, the peptide consisting of an amino acid sequence of SEQ ID NO: 1, 2, 3, or 4 was found to exhibit effects of promoting proliferation by activation of MAPK (ERK, p38, and JNK) and AKT, i.e., signaling factors involved in proliferation of fibroblasts.

3-2. Keratinocytes

Human keratinocyte HaCaT was seeded in a 6-well plate at a density of $3 \times 10^5$ cells/well, and then cultured overnight. Subsequently, the media were changed to 0.05% FBS-containing media. Then, treatment with the positive control, i.e., 10 nM EGF, and 10 μM or 50 μM of the peptide consisting of an amino acid sequence of SEQ ID NO: 1 or 2 were performed and cultured for 30 minutes. Then, the cells were collected to prepare cell lysate. Then, western blotting was performed using P-MAPK (p-Erk, p-JNK, p-p38) and p-Akt antibody (Santacruz Biotechnology, USA). The comparison results of phosphorylation aspects thereof are shown in FIGS. 13 and 14.

Figure 13:
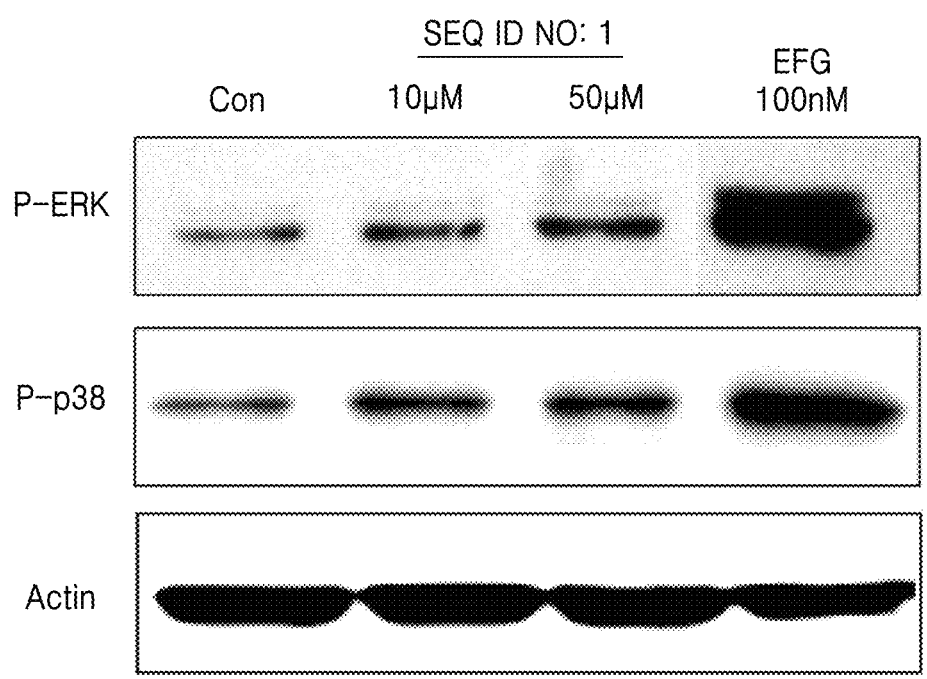
FIG. 13 is an image showing measurement results of phosphorylation level of MAPK (AKT elimination) in keratinocytes of a peptide consisting of an amino acid sequence of SEQ ID NO: 1 according to an embodiment the present disclosure.
Figure 14:
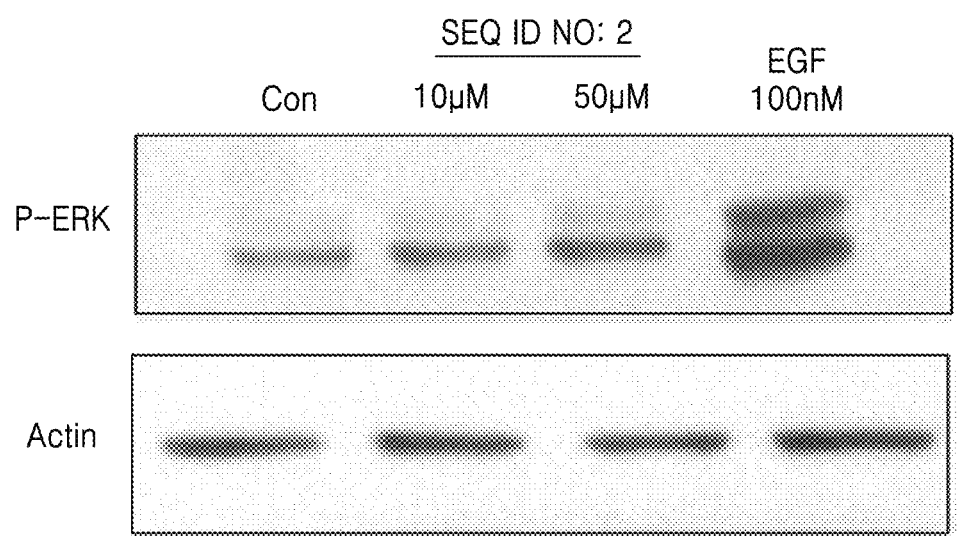
FIG. 14 is an image showing measurement results of phosphorylation level of MAPK (AKT elimination) in keratinocytes of a peptide consisting of an amino acid sequence of SEQ ID NO: 2 according to an embodiment the present disclosure.
Figure 15:
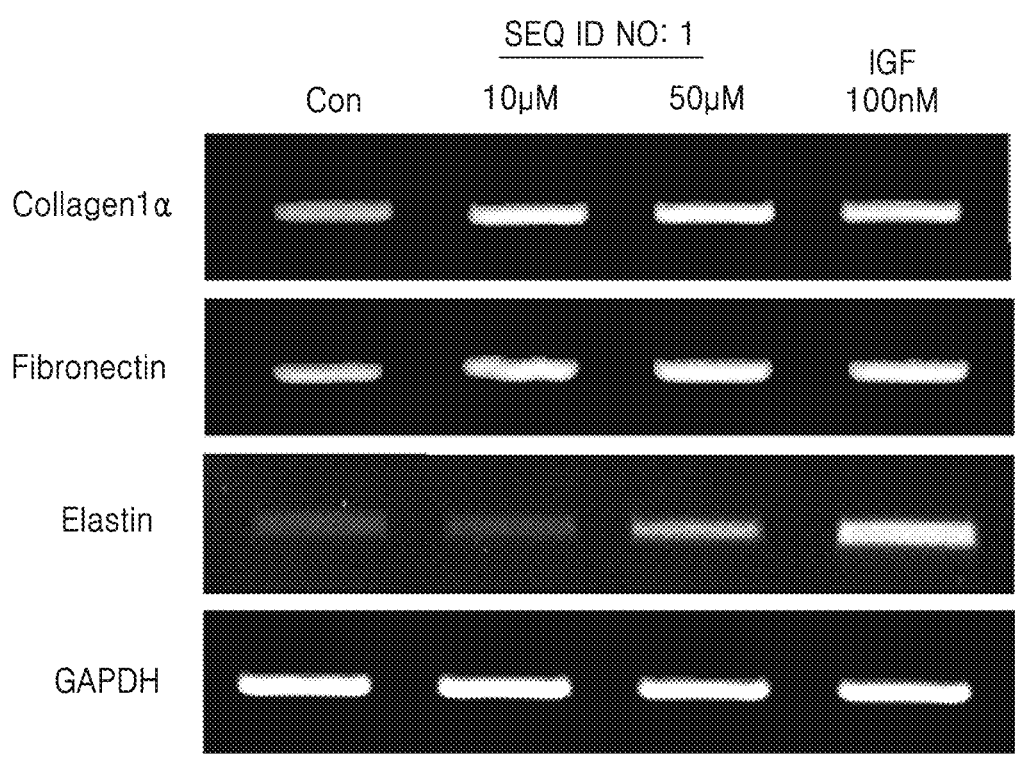
FIG. 15 is an image showing results of collagen1a, fibronectin and elastin RT-PCR of a peptide consisting of an amino acid sequence of SEQ ID NO: 1 according to the embodiment of the present disclosure.
Figure 16:
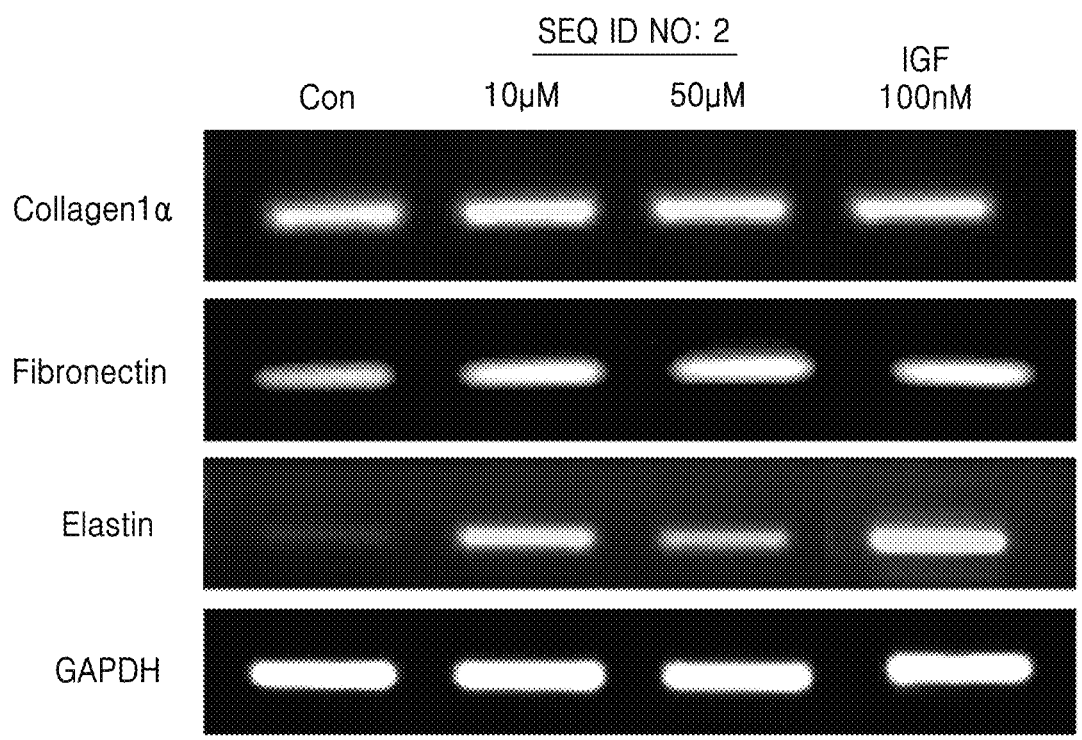
FIG. 16 is an image showing results of collagen1a, fibronectin and elastin RT-PCR of a peptide consisting of an amino acid sequence of SEQ ID NO: 2 according to the embodiment of the present disclosure.
Figure 17:
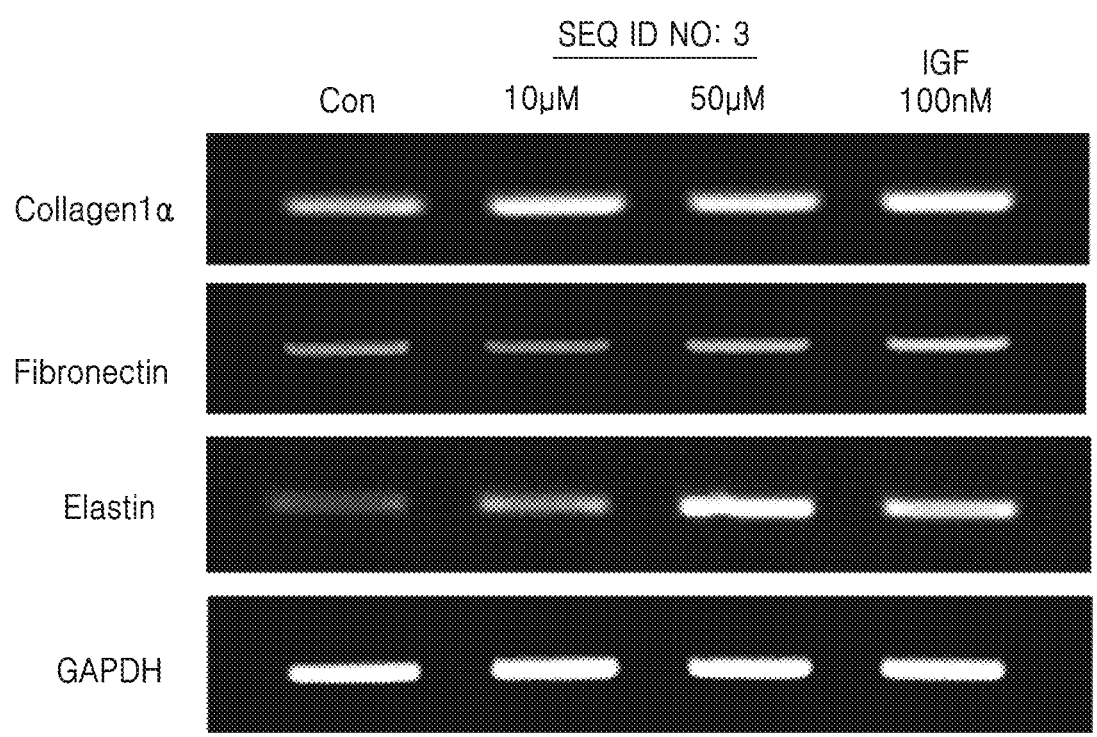
FIG. 17 is an image showing results of collagen1a, fibronectin and elastin RT-PCR of a peptide consisting of an amino acid sequence of SEQ ID NO: 3 according to the embodiment of the present disclosure.
Figure 18:
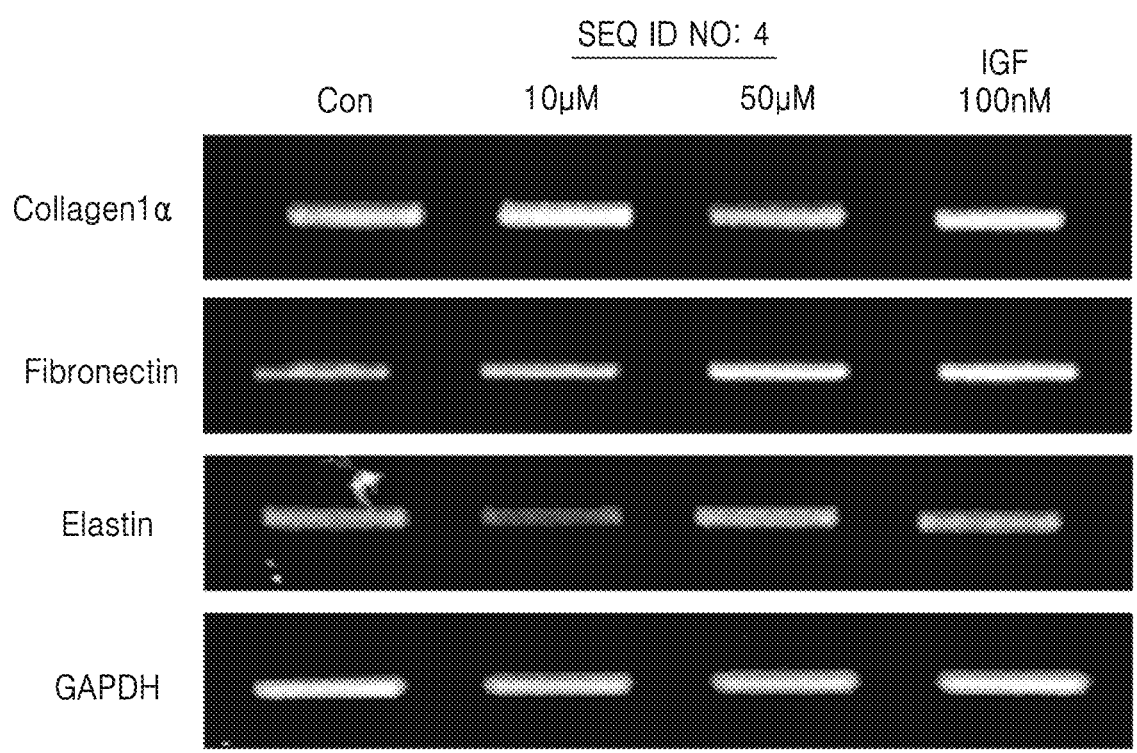
FIG. 18 is an image showing results of collagen1a, fibronectin and elastin RT-PCR of a peptide consisting of an amino acid sequence of SEQ ID NO: 4 according to the embodiment of the present disclosure.

As shown in FIGS. 13 and 14, the peptide consisting of an amino acid sequence of SEQ ID NO: 1 or 2 was found to exhibit effects of promoting proliferation by activation of ERK and p38, i.e., signaling factors involved in proliferation of human keratinocytes.

Example 4. RT-PCR of Collagen1a, Fibronectin, and Elastin

Mouse fibroblast NIH3T3 was seeded in a 6-well plate at a density of $5 \times 10^3$ cells/well, and then cultured overnight. Subsequently, the media were changed to 0.05% FBS-containing media, followed by culturing for 4 hours. Then, treatment with the positive control, i.e., 100 nM IGF-1, and 10 μM or 50 μM of the peptide consisting of an amino acid sequence of SEQ ID NO: 1, 2, 3, or 4 were performed and cultured for 24 hours. Then, the cells were cultured and collected to isolate RNA. cDNA was synthesized using a cDNA synthesis kit (Intron, Korea) after quantification of RNA, and PCR was carried out using primers of each of PCR premix (Intron, Korea) and collagen1a, fibronectin, elastin, GAPDH in Table 4. Then, the cells were run on 5% agarose gel, and degrees of mRNA expression of the growth factors were compared in each peptide treatment condition. The results are shown in FIGS. 15 to 18.

TABLE 4

| Sequence ID No. | Primer | Sequence (5'-3') |
|---|---|---|
| 5 | Collagen1a_F | CACCCTCAAGAGCCTGAGTC |
| 6 | Collagen1a_R | AGACGGCTGAGTAGGGAACA |
| 7 | Fibronectin_F | CCAGGAACCGAGTACACCAT |
| 8 | Fibronectin_R | ATACCCAGGTTGGGTGATGA |
| 9 | Elastin_F | GGACCCCTGACTCGCGACCT |
| 10 | Elastin_R | GGGGAGGTGGGACTGCCCAA |
| 11 | GAPDH_F | GGTGTGAACGGATTTGGCCGTATTG |
| 12 | GAPDH_R | CCGTTGAATTTGCCGTGAGTGGAGT |

As shown in FIGS. 15 to 18, the peptide consisting of an amino acid sequence of SEQ ID NO: 1, 2, 3, or 4 shows effects of increasing expression of mRNA of collagen, fibronectin, and elastin as constituents of ECM through promoting fibroblast activity, respectively.

Example 5. RT-PCR of AQP3 (Aquaporin3) and SIRT1

Human keratinocyte HaCaT was seeded in a 6-well plate at a density of $3 \times 10^5$ cells/well, and then cultured overnight. Subsequently, the media were changed to 0.05% FBS-containing media, followed by culturing for 4 hours. Then, treatment with the positive control, i.e., 100 nM EGF, and 10 μM or 50 μM of the peptide consisting of an amino acid sequence of SEQ ID NO: 1 or 2 were performed and cultured for 24 hours. Then, the cells were cultured and collected to isolate RNA. cDNA was synthesized using a cDNA synthesis kit (Intron, Korea) after quantification of RNA, and PCR was carried out using primers of each of PCR premix (Intron, Korea) and AQP3, SIRT1, and GAPDH in Table 5. Then, the cells were run on 5% agarose gel, and degrees of mRNA expression of the growth factors were compared in each peptide treatment condition. The results are shown in FIGS. 19 to 21.

TABLE 5

| Sequence ID No. | Primer | Sequence (5'-3') |
|---|---|---|
| 13 | AQP3_F | CCTTCTTGGGTGCTGGAATA |
| 14 | AQP3_R | ACACGATAAGGGAGGCTCTG |
| 15 | SIRT1_F | TCAGTGGCTGGAACAGTGAG |
| 16 | SIRT1_R | TCTGGCATGTCCCACTATCA |

Figure 19:
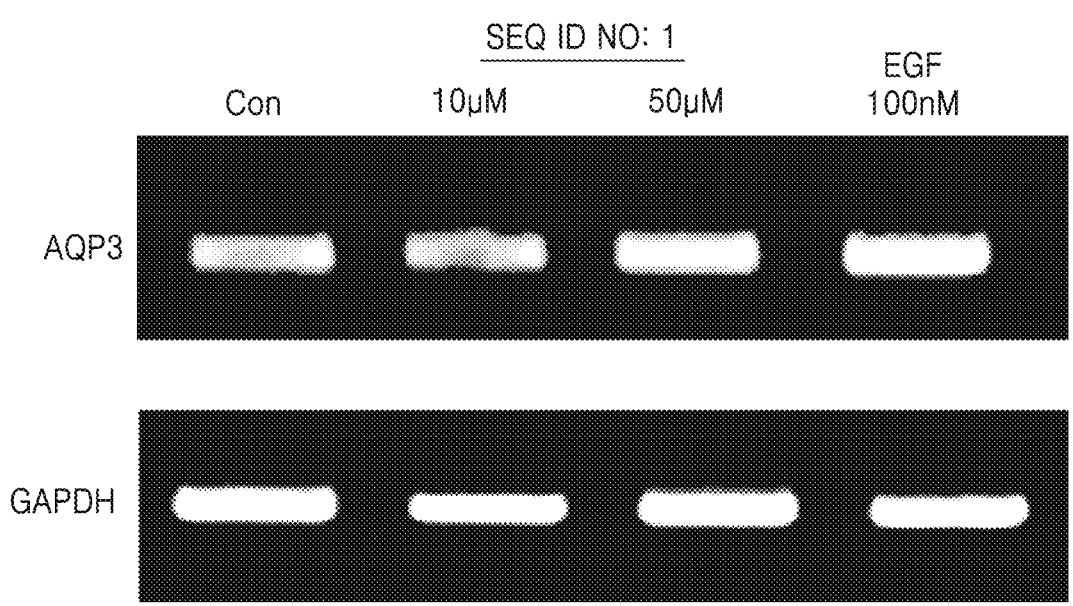
FIG. 19 is an image showing results of AQP3 (Aquaporin 3) RT-PCR of a peptide consisting of an amino acid sequence of SEQ ID NO: 1 according to the embodiment of the present disclosure.
Figure 20:
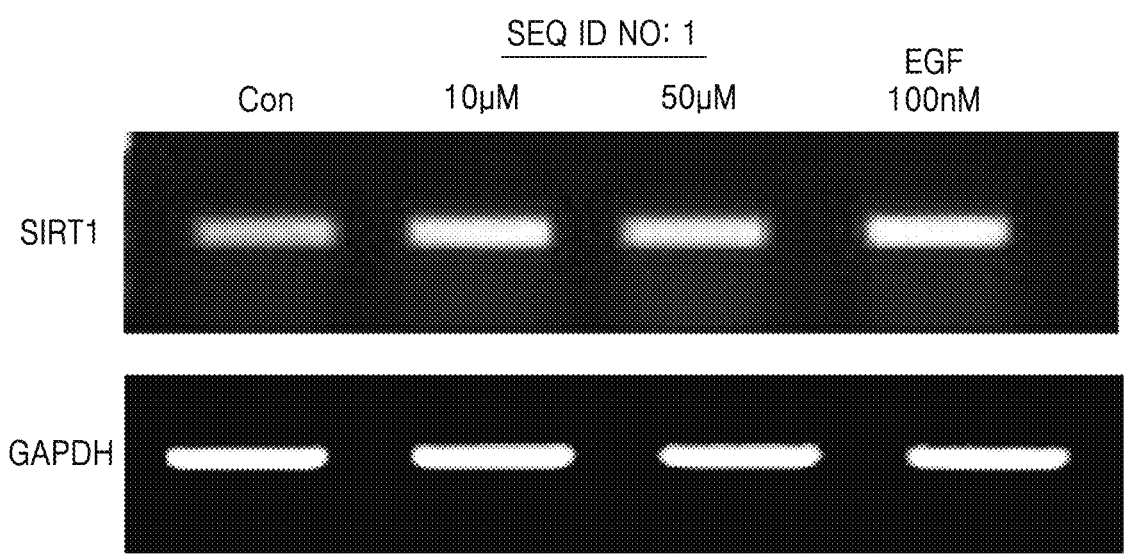
FIG. 20 is an image showing results of SIRT1 RT-PCR of a peptide consisting of an amino acid sequence of SEQ ID NO: 1 according to the embodiment of the present disclosure.
Figure 21:
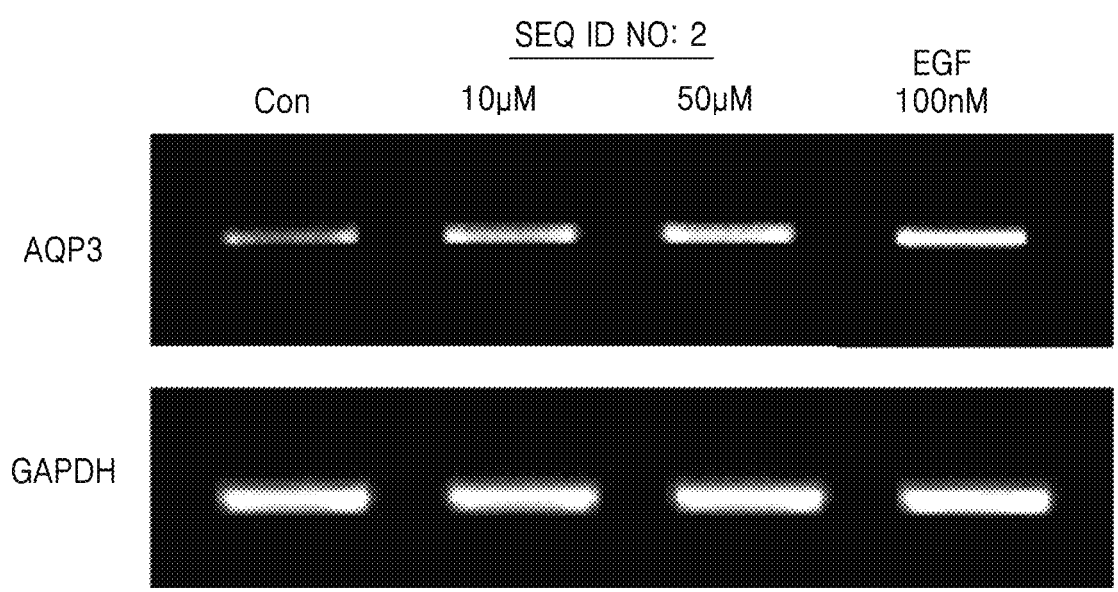
FIG. 21 is an image showing results of AQP3 (Aquaporin 3) RT-PCR of a peptide consisting of an amino acid sequence of SEQ ID NO: 2 according to the embodiment of the present disclosure.
Figure 22:
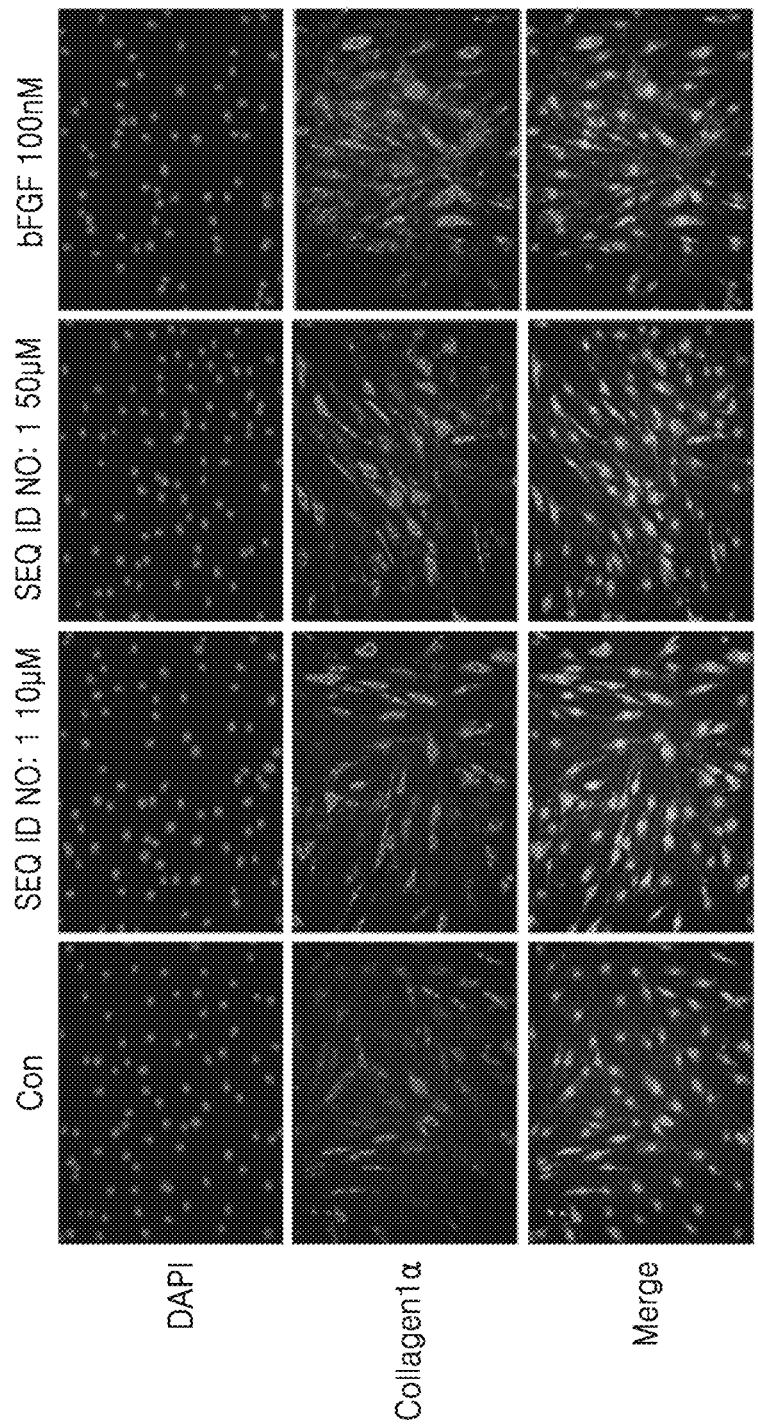
FIG. 22 is an image showing measurement results of an expression amount of collagen1a of a peptide consisting of an amino acid sequence of SEQ ID NO: 1 according to the embodiment of the present disclosure.
Figure 23:
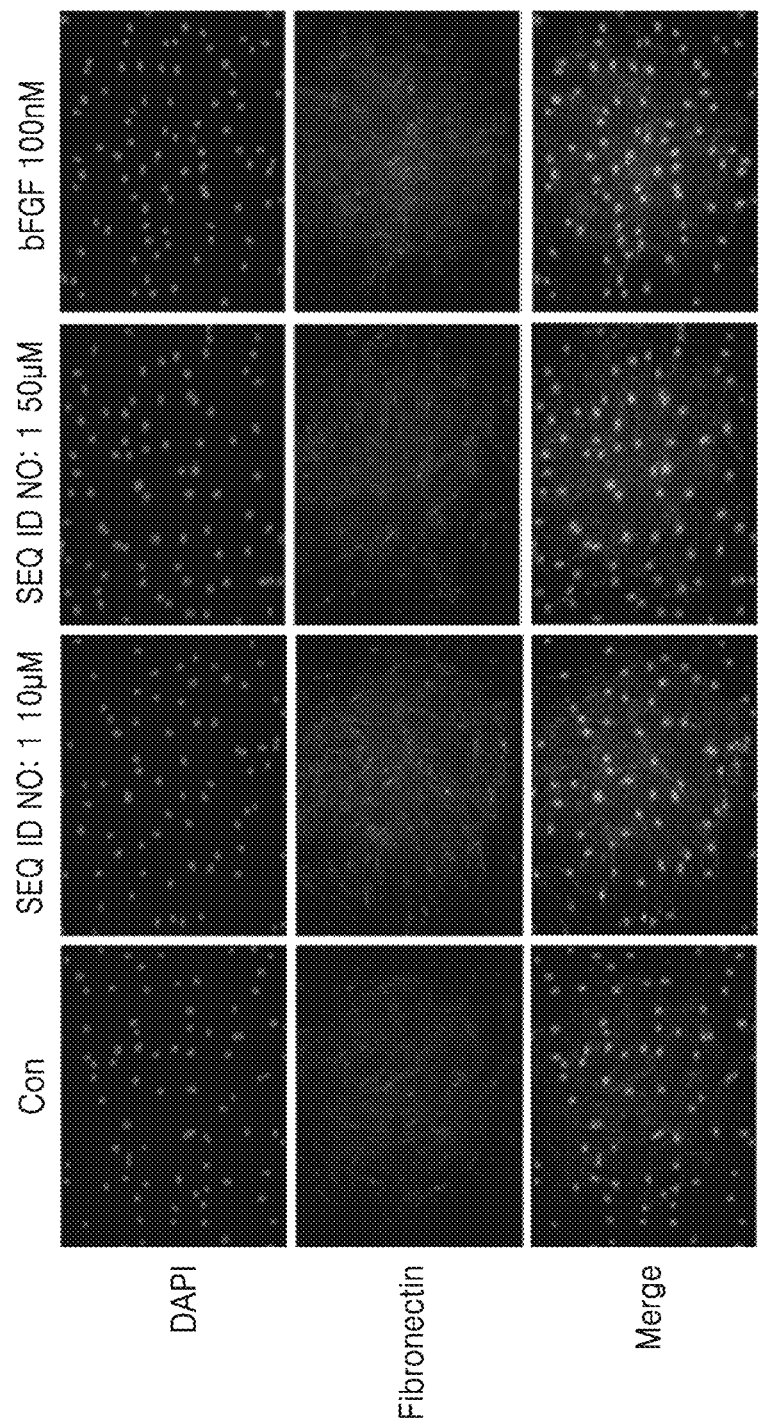
FIG. 23 is an image showing measurement results of an expression amount of fibronectin of a peptide consisting of an amino acid sequence of SEQ ID NO: 1 according to the embodiment of the present disclosure.
Figure 24:
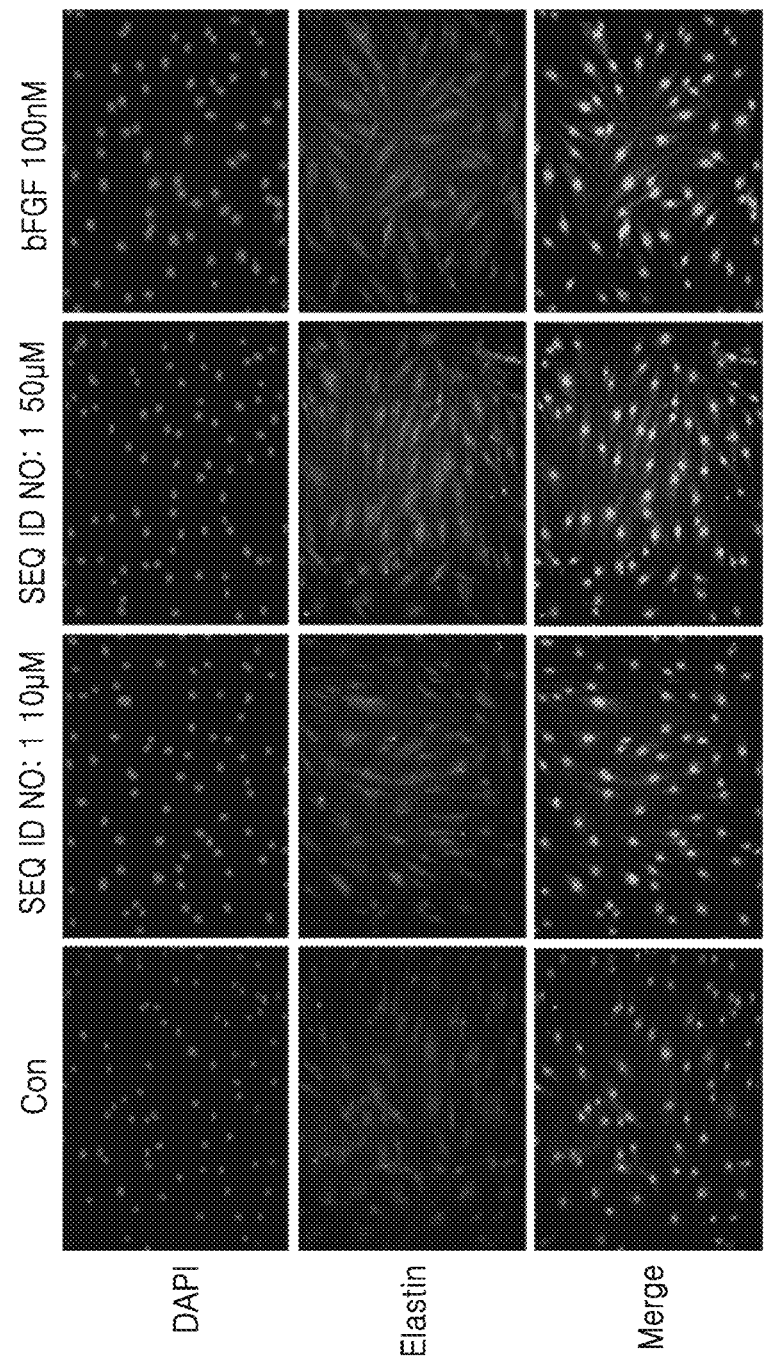
FIG. 24 is an image showing measurement results of an expression amount of elastin of a peptide consisting of an amino acid sequence of SEQ ID NO: 1 according to the embodiment of the present disclosure.
Figure 25:
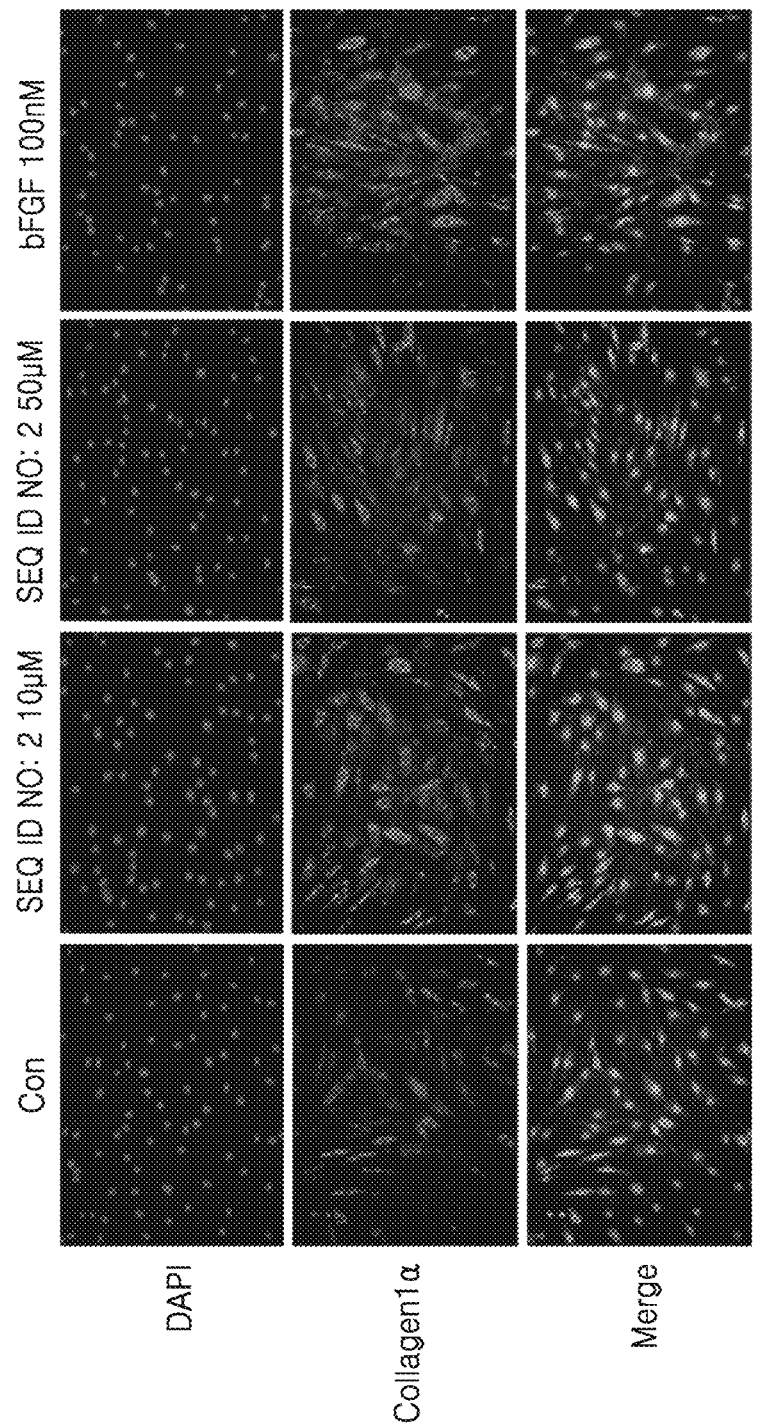
FIG. 25 is an image showing measurement results of an expression amount of collagen1a of a peptide consisting of an amino acid sequence of SEQ ID NO: 2 according to the embodiment of the present disclosure.
Figure 26:
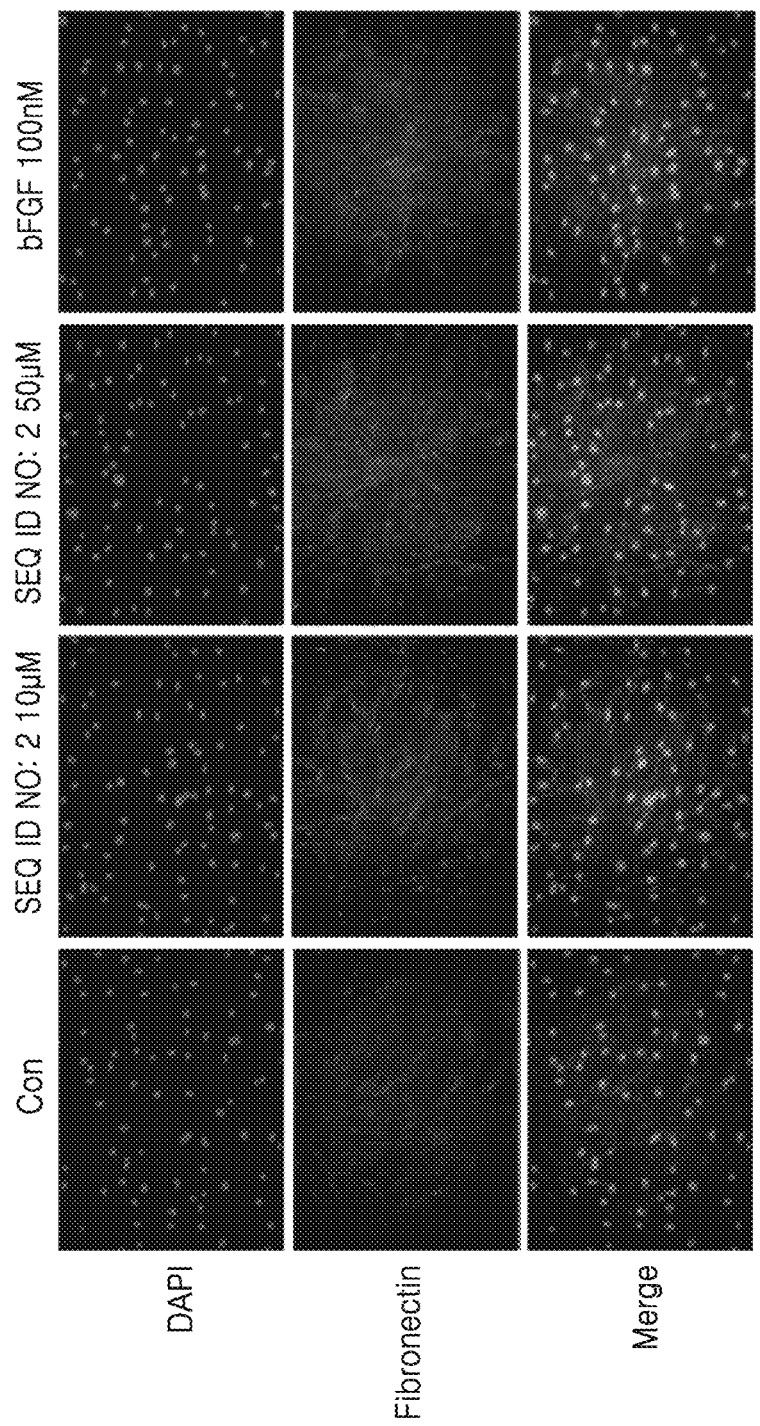
FIG. 26 is an image showing measurement results of an expression amount of fibronectin of a peptide consisting of an amino acid sequence of SEQ ID NO: 2 according to the embodiment of the present disclosure.
Figure 27:
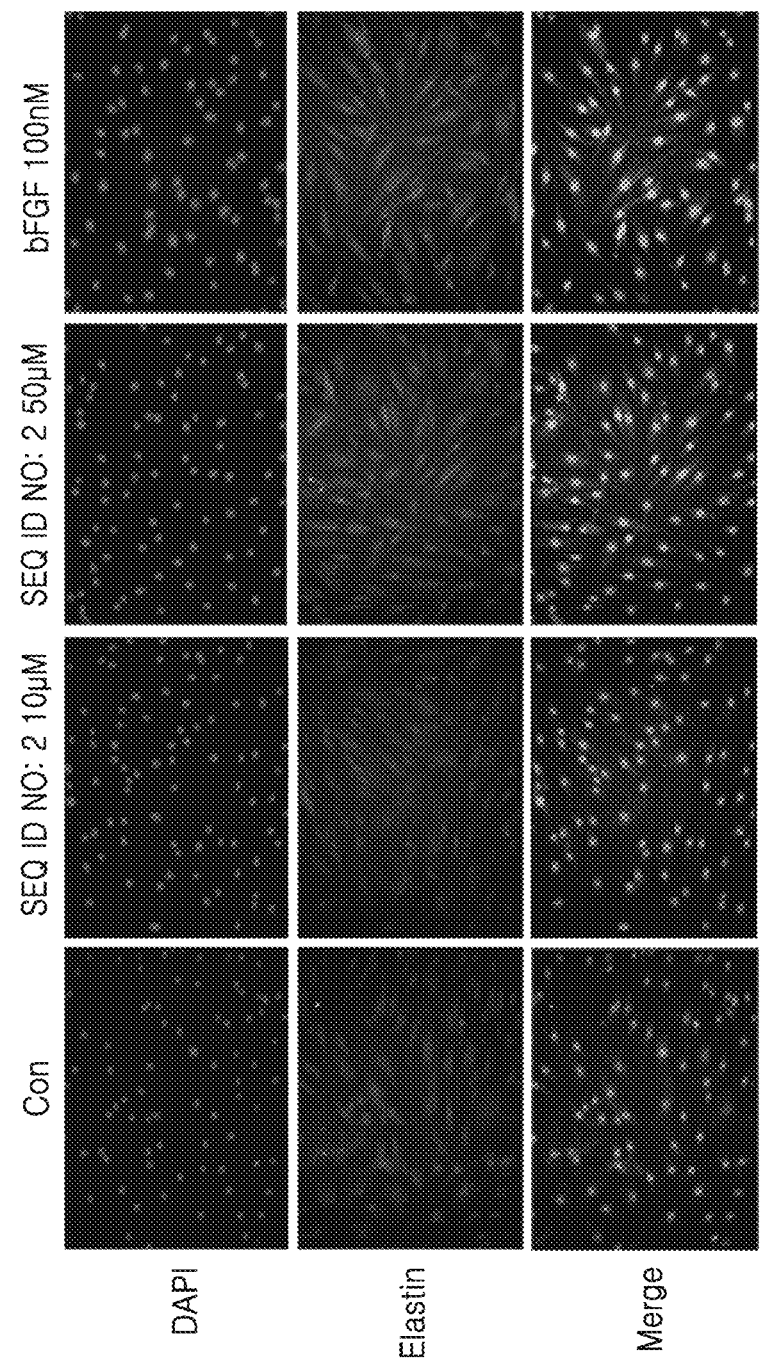
FIG. 27 is an image showing measurement results of an expression amount of elastin of a peptide consisting of an amino acid sequence of SEQ ID NO: 2 according to the embodiment of the present disclosure.

As shown in FIGS. 19 to 21, the peptide consisting of an amino acid sequence of SEQ ID NO: 1 or 2 shows effects of increasing AQP3 expression, which is a protein related to skin barrier enhancement through promotion of keratinocyte activation.

Example 6. RT-PCR of Collagen1a, Fibronectin, and Elastin

Mouse fibroblast NIH3T3 was seeded in a 6-well plate at a density of $5 \times 10^3$ cells/well, and then cultured overnight.

Subsequently, the media were changed to 0.05% serum-free media. Then, treatment with the positive control, i.e., 100 nM EGF, and the peptide consisting of an amino acid sequence of SEQ ID NO: 1 or 2 were performed and cultured for 24 hours. Then, the cells were fixed for 30 minutes using 4% paraformaldehyde. Then, after washing 3 times, the cells were reacted with 0.5% Triton X-100 for 15 minutes and washed again 3 times. Then, 3% BSA was blocked for 1 hour and the primary antibody (1:100) for collagen 1a, fibronectin, and elastin was reacted overnight at 4° C. Then, the secondary antibody (1:500) was reacted at room temperature for 2 hours, stained with DAPI staining, and observation was made with a fluorescence microscope. The results thereof are shown in FIGS. 22 to 27.

As shown in FIGS. 22 to 27, the peptide consisting of an amino acid sequence of SEQ ID NO: 1 or 2 shows effects of increasing expression of proteins of collagen, fibronectin, and elastin as constituents of ECM through promoting fibroblast activity, respectively.

Example 7. Procollagen1a ELISA

Mouse fibroblast NIH3T3 was seeded in a 6-well plate at a density of 5×10$^3$ cells/well, and then cultured overnight. Subsequently, the media were changed to 0.05% FBS-containing media, followed by culturing for 4 hours. Then, treatment with the positive control, i.e., 100 nM IGF-1, and the peptide consisting of an amino acid sequence of SEQ ID NO: 1, 2, 3, or 4 were performed and cultured for 72 hours. Then, the media were collected. The amount in the medium was measured using Procollagen1a ELISA kit (Usbiological Lifescience, USA). The results thereof are shown in FIGS. 28 to 31 and Table 6.

TABLE 6

Figure 28:
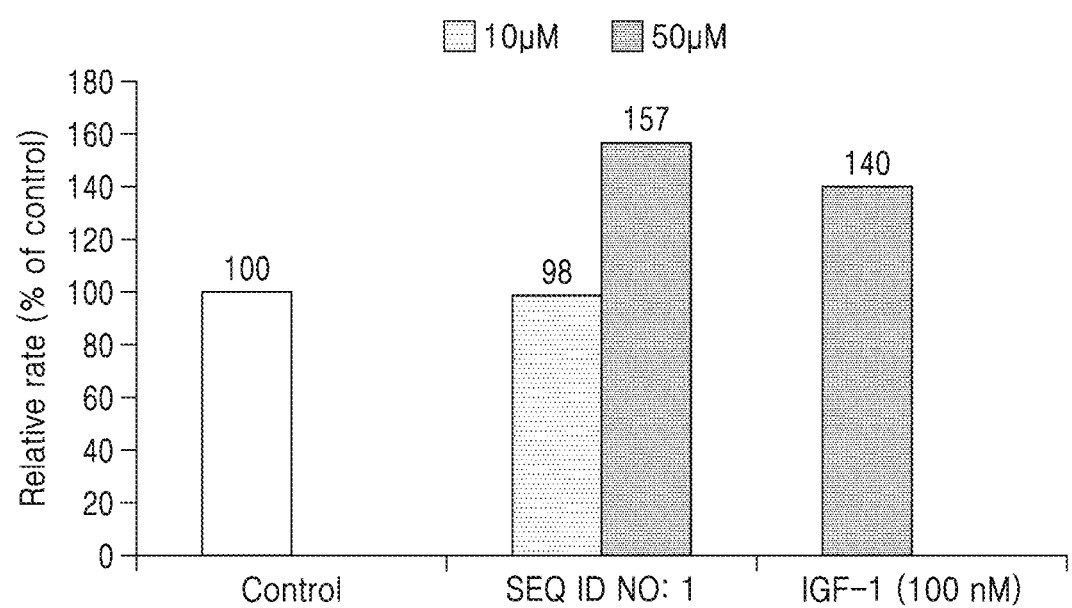
FIG. 28 is an image showing results of Procollagen1a ELISA of a peptide consisting of an amino acid sequence of SEQ ID NO: 1 according to the embodiment of the present disclosure.
Figure 29:
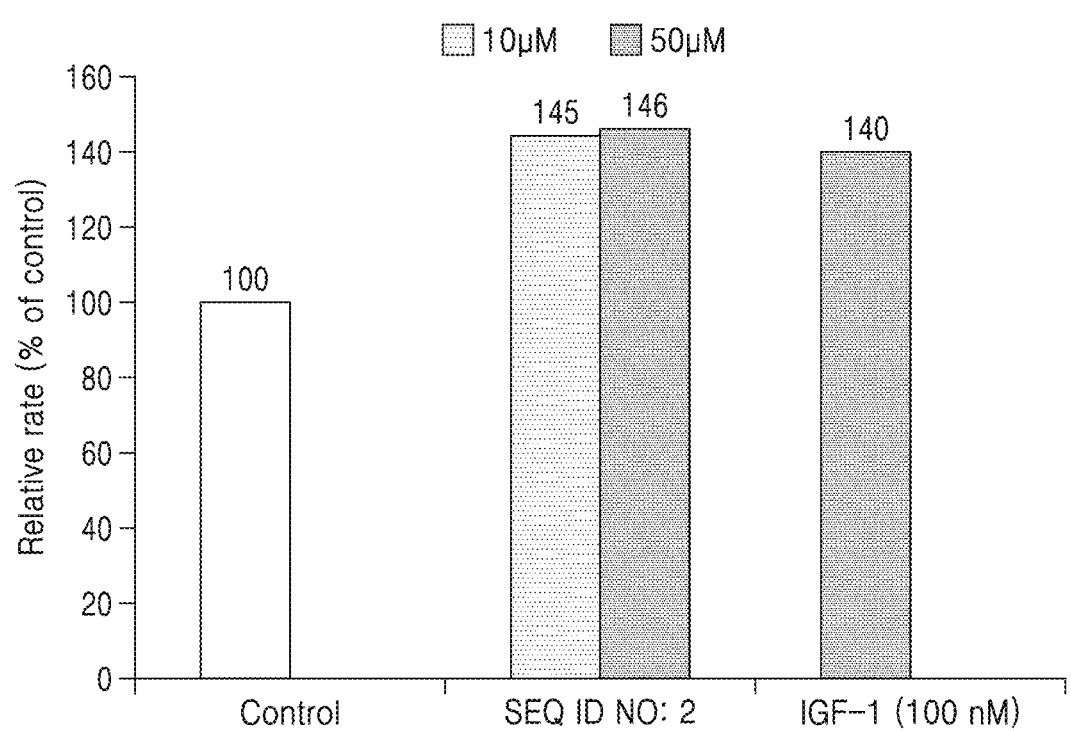
FIG. 29 is an image showing results of Procollagen1a ELISA of a peptide consisting of an amino acid sequence of SEQ ID NO: 2 according to the embodiment of the present disclosure.
Figure 30:
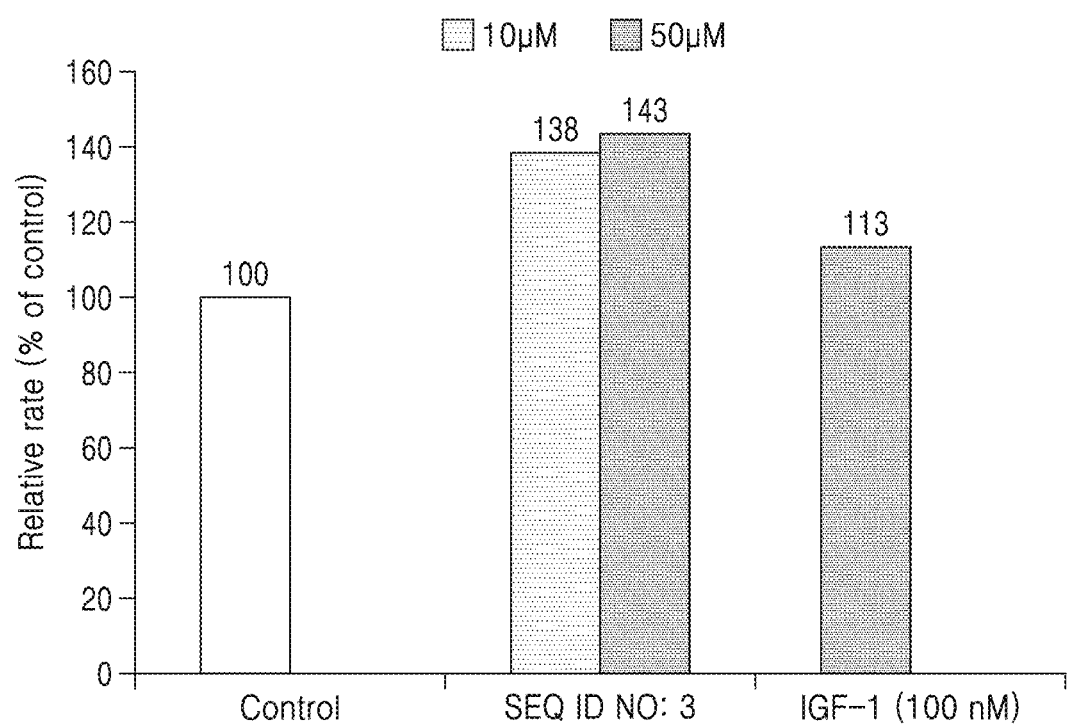
FIG. 30 is an image showing results of Procollagen1a ELISA of a peptide consisting of an amino acid sequence of SEQ ID NO: 3 according to the embodiment of the present disclosure.

| | Procollagen1a expression (%) | | | |
|---|---|---|---|---|
| FIG. 28 | Control | SEQ ID NO: 1 | | IGF-1 |
| | | 10 μM | 50 μM | (100 nM) |
| | 100 | 98 | 157 | 140 |
| FIG. 29 | Control | SEQ ID NO: 2 | | IGF-1 |
| | | 10 μM | 50 μM | (100 nM) |
| | 100 | 145 | 146 | 140 |
| FIG. 30 | Control | SEQ ID NO: 3 | | IGF-1 |
| | | 10 μM | 50 μM | (100 nM) |
| | 100 | 138 | 143 | 113 |

TABLE 6-continued

Figure 31:
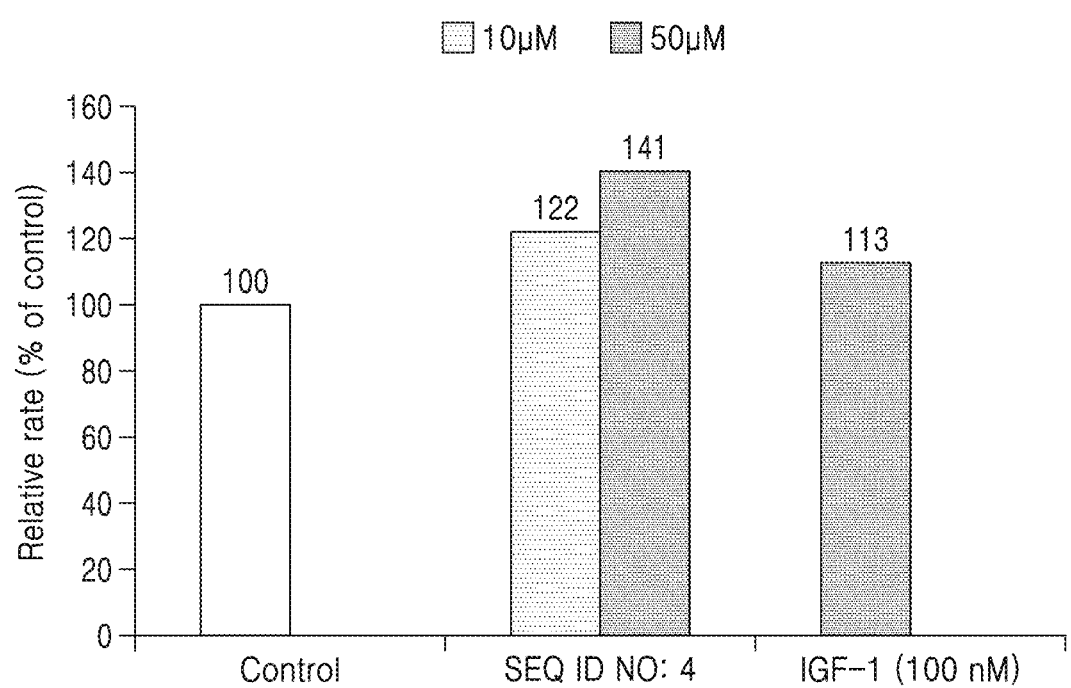
FIG. 31 is an image showing results of Procollagen1a ELISA of a peptide consisting of an amino acid sequence of SEQ ID NO: 4 according to the embodiment of the present disclosure.

| | Procollagen1a expression (%) | | | |
|---|---|---|---|---|
| FIG. 31 | Control | SEQ ID NO: 4 | | IGF-1 |
| | | 10 μM | 50 μM | (100 nM) |
| | 100 | 122 | 141 | 113 |

As shown in FIGS. 28 to 31 and Table 6, upon treatment with the peptide consisting of an amino acid sequence of SEQ ID NO: 1, 2, 3, or 4, expression of pro-collagen1α protein was found to increase in fibroblasts.

Example 8. HA ELISA

Human keratinocyte HaCaT was seeded in a 6-well plate at a density of 3×10$^5$ cells/well, and then cultured overnight. The media were changed to 0.05% FBS-containing media, followed by culturing for 4 hours. Then, treatment with the positive control, i.e., 100 nM IGF-1, and the peptide consisting of an amino acid sequence of SEQ ID NO: 2 were performed and cultured for 72 hours. Then, the media were collected. An HA ELISA kit (Echelon, USA) was used to measure an amount thereof. The results thereof are shown in FIG. 32 and Table 7.

TABLE 7

Figure 32:
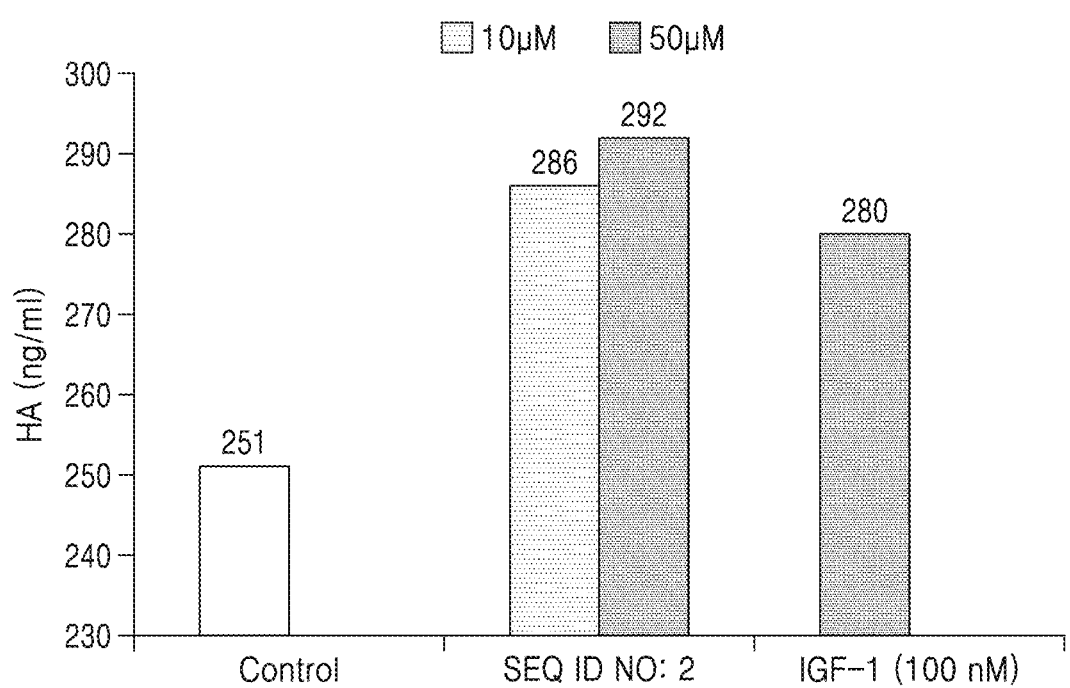
FIG. 32 is an image showing results of HA ELISA of a peptide consisting of an amino acid sequence of SEQ ID NO: 2 according to the embodiment of the present disclosure.

| | HA expression (ng/mL) | | | |
|---|---|---|---|---|
| FIG. 32 | Control | SEQ ID NO: 2 | | IGF-1 |
| | | 10 μM | 50 μM | (100 nM) |
| | 251 | 286 | 292 | 280 |

As shown in FIG. 32 and Table 7, the peptide consisting of an amino acid sequence of SEQ ID NO: 2 shows effects of increasing HA expression, which is a protein related to skin barrier enhancement through promotion of keratinocyte activation.

INDUSTRIAL APPLICABILITY

The present disclosure relates to a peptide consisting of an amino acid sequence of SEQ ID NO: 1, 2, 3, or 4, a pharmaceutical composition for preventing or treating skin disease including the peptide, a cosmetic composition for skin condition improvement including the peptide, a food composition for skin condition improvement including the peptide, a method of preventing or treating skin disease using the peptide, and a use of the peptide in preventing or treating skin disease or improving skin condition.

The invention claimed is:

1. A method of improving a skin condition of a subject, the method comprising administering a peptide consisting of the amino acid sequence of SEQ ID NO: 2 to the subject, optionally wherein (a) the N-terminus of the peptide is linked to a protecting group, or (b) the C-terminus of the peptide is modified.

2. The method of claim 1, wherein (a) the N-terminus of the peptide is linked to a protecting group, which is optionally selected from the group consisting of an acetyl group, a fluorenylmethoxycarbonyl group, a formyl group, a palmitoyl group, a myristyl group, a stearyl group, and a polyethylene glycol (PEG), or (b) the C-terminus of the peptide is modified, optionally by being linked to a group selected from the group consisting of an amino group (—NH$_2$) and an azide group (—NHNH$_2$).

3. The method of claim 1, wherein the skin condition improvement is wrinkle improvement, skin regeneration, skin elasticity improvement, wound regeneration, acne improvement, or skin whitening.

4. A method of improving a skin condition of a subject, the method comprising contacting the skin of the subject with a cosmetic composition for skin condition improvement comprising a peptide consisting of the amino acid sequence of SEQ ID NO: 2, optionally wherein (a) the N-terminus of the peptide is linked to a protecting group, or (b) the C-terminus of the peptide is modified.

5. The method of claim 4, wherein (a) the N-terminus of the peptide is linked to a protecting group, which is optionally selected from the group consisting of an acetyl group, a fluorenylmethoxycarbonyl group, a formyl group, a palmitoyl group, a myristyl group, a stearyl group, and a polyethylene glycol (PEG), or (b) the C-terminus of the peptide is modified, optionally by being linked to a group selected from the group consisting of a hydroxyl group (OH), an amino group (—NH$_2$) and an azide group (—NHNH$_2$).

6. The method of claim 4, wherein the skin condition improvement is wrinkle improvement, skin regeneration, skin elasticity improvement, wound regeneration, acne improvement, or skin whitening.

7. A method of treating a skin disease in a subject, the method comprising administering a pharmaceutical composition for treating skin disease comprising a peptide consisting of the amino acid sequence of SEQ ID NO: 2 to the subject, optionally wherein (a) the N-terminus of the peptide is linked to a protecting group, or (b) the C-terminus of the peptide is modified.

8. The method of claim 7, wherein (a) the N-terminus of the peptide is linked to a protecting group, which is optionally selected from the group consisting of an acetyl group, a fluorenylmethoxycarbonyl group, a formyl group, a palmitoyl group, a myristyl group, a stearyl group, and a polyethylene glycol (PEG), or (b) the C-terminus of the peptide is modified, optionally by being linked to a group selected from the group consisting of an amino group (—NH$_2$) and an azide group (—NHNH$_2$).

9. The method of claim 7, wherein the skin disease is psoriasis, atopic dermatitis, non-allergic dermatitis, or xeroderma.

10. A method of improving a skin condition of a subject, the method comprising administering a food composition for skin condition improvement comprising a peptide consisting of the amino acid sequence of SEQ ID NO: 2 to the subject, optionally wherein (a) the N-terminus of the peptide is linked to a protecting group, or (b) the C-terminus of the peptide is modified.

11. The method of claim 10, wherein (a) the N-terminus of the peptide is linked to a protecting group, which is optionally selected from the group consisting of an acetyl group, a fluorenylmethoxycarbonyl group, a formyl group, a palmitoyl group, a myristyl group, a stearyl group, and a polyethylene glycol (PEG), or (b) the C-terminus of the peptide is modified, optionally by being linked to a group selected from the group consisting of an amino group (—NH$_2$) and an azide group (—NHNH$_2$).

12. The method of claim 10, wherein the skin condition improvement is wrinkle improvement, skin regeneration, skin elasticity improvement, wound regeneration, acne improvement, or skin whitening.

* * * * *

SEQUENCE LISTING

<160> NUMBER OF SEQ ID NOS: 16

<210> SEQ ID NO 1
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1

Lys Trp Gly Gly Gly Arg Tyr
1               5

<210> SEQ ID NO 2
<211> LENGTH: 7
<212> TYPE: PRT

<213> ORGANISM: Artificial Sequence
<220> FEATURE:
<223> OTHER INFORMATION: Synthetic Construct

<400> SEQUENCE: 2

Ile Leu Gly Arg Trp Cys Gly
1               5

<210> SEQ ID NO 3
<211> LENGTH: 4
<212> TYPE: PRT
<213> ORGANISM: Artificial Sequence
<220> FEATURE:
<223> OTHER INFORMATION: Synthetic Construct

<400> SEQUENCE: 3

Gly Pro Val His
1

<210> SEQ ID NO 4
<211> LENGTH: 11
<212> TYPE: PRT
<213> ORGANISM: Artificial Sequence
<220> FEATURE:
<223> OTHER INFORMATION: Synthetic Construct

<400> SEQUENCE: 4

Glu Asp Glu Phe Lys Pro Pro Ala Ala Gly Arg
1               5                   10

<210> SEQ ID NO 5
<211> LENGTH: 20
<212> TYPE: DNA
<213> ORGANISM: Artificial Sequence
<220> FEATURE:
<223> OTHER INFORMATION: Synthetic Construct

<400> SEQUENCE: 5
caccctcaag agcctgagtc                                              20

<210> SEQ ID NO 6
<211> LENGTH: 20
<212> TYPE: DNA
<213> ORGANISM: Artificial Sequence
<220> FEATURE:
<223> OTHER INFORMATION: Synthetic Construct

<400> SEQUENCE: 6
agacggctga gtagggaaca                                              20

<210> SEQ ID NO 7
<211> LENGTH: 20
<212> TYPE: DNA
<213> ORGANISM: Artificial Sequence
<220> FEATURE:
<223> OTHER INFORMATION: Synthetic Construct

<400> SEQUENCE: 7
ccaggaaccg agtacaccat                                              20

<210> SEQ ID NO 8
<211> LENGTH: 20
<212> TYPE: DNA
<213> ORGANISM: Artificial Sequence
<220> FEATURE:
<223> OTHER INFORMATION: Synthetic Construct

```
<400> SEQUENCE: 8
atacccaggt tgggtgatga                                              20

<210> SEQ ID NO 9
<211> LENGTH: 20
<212> TYPE: DNA
<213> ORGANISM: Artificial Sequence
<220> FEATURE:
<223> OTHER INFORMATION: Synthetic Construct

<400> SEQUENCE: 9
ggacccctga ctcgcgacct                                              20

<210> SEQ ID NO 10
<211> LENGTH: 20
<212> TYPE: DNA
<213> ORGANISM: Artificial Sequence
<220> FEATURE:
<223> OTHER INFORMATION: Synthetic Construct

<400> SEQUENCE: 10
ggggaggtgg gactgcccaa                                              20

<210> SEQ ID NO 11
<211> LENGTH: 25
<212> TYPE: DNA
<213> ORGANISM: Artificial Sequence
<220> FEATURE:
<223> OTHER INFORMATION: Synthetic Construct

<400> SEQUENCE: 11
ggtgtgaacg gatttggccg tattg                                        25

<210> SEQ ID NO 12
<211> LENGTH: 25
<212> TYPE: DNA
<213> ORGANISM: Artificial Sequence
<220> FEATURE:
<223> OTHER INFORMATION: Synthetic Construct

<400> SEQUENCE: 12
ccgttgaatt tgccgtgagt ggagt                                        25

<210> SEQ ID NO 13
<211> LENGTH: 20
<212> TYPE: DNA
<213> ORGANISM: Artificial Sequence
<220> FEATURE:
<223> OTHER INFORMATION: Synthetic Construct

<400> SEQUENCE: 13
ccttcttggg tgctggaata                                              20

<210> SEQ ID NO 14
<211> LENGTH: 20
<212> TYPE: DNA
<213> ORGANISM: Artificial Sequence
<220> FEATURE:
<223> OTHER INFORMATION: Synthetic Construct

<400> SEQUENCE: 14
acacgataag ggaggctctg                                              20

<210> SEQ ID NO 15
<211> LENGTH: 20
```

```
<212> TYPE: DNA
<213> ORGANISM: Artificial Sequence
<220> FEATURE:
<223> OTHER INFORMATION: Synthetic Construct

<400> SEQUENCE: 15
tcagtggctg gaacagtgag                                              20

<210> SEQ ID NO 16
<211> LENGTH: 20
<212> TYPE: DNA
<213> ORGANISM: Artificial Sequence
<220> FEATURE:
<223> OTHER INFORMATION: Synthetic Construct

<400> SEQUENCE: 16
tctggcatgt cccactatca                                              20
```